United States Patent [19]

Levy et al.

[11] Patent Number: 5,492,753
[45] Date of Patent: Feb. 20, 1996

[54] STRETCHABLE MELTBLOWN FABRIC WITH BARRIER PROPERTIES

[75] Inventors: Ruth L. Levy, Sugar Hill; Charles E. Bolian, II, Buford; Michael T. Morman, Alpharetta; Lynn E. Preston, Atlanta, all of Ga.

[73] Assignee: Kimberly-Clark Corporation, Neenah, Wis.

[21] Appl. No.: 164,652

[22] Filed: Dec. 8, 1993

Related U.S. Application Data

[63] Continuation of Ser. No. 990,161, Dec. 14, 1992, abandoned.

[51] Int. Cl.$^6$ ............................ B32B 5/26; D04H 3/00; D04H 3/16
[52] U.S. Cl. .................. 428/219; 2/2; 2/77; 2/79; 2/93; 2/115; 2/243.1; 264/288.4; 264/291; 264/348; 428/236; 428/237; 428/283; 428/286; 428/287; 428/288; 428/296; 428/298; 428/311.5; 428/903
[58] Field of Search ................................ 2/2, 79, 77, 93, 2/115, 243.1; 264/288.4, 291, 348; 428/236, 237, 286, 283, 287, 288, 296, 298, 311.5, 903, 219

[56] References Cited

U.S. PATENT DOCUMENTS

| | | | |
|---|---|---|---|
| 1,741,530 | 12/1929 | Mayer . | |
| 2,971,322 | 2/1961 | Bouvet | 57/140 |
| 3,047,444 | 7/1962 | Harwood | 154/46 |
| 3,059,313 | 10/1962 | Harmon | 28/80 |
| 3,256,258 | 6/1966 | Herrman . | |
| 3,396,071 | 8/1968 | Couzens . | |
| 3,406,033 | 10/1968 | Reitz . | |
| 3,438,844 | 4/1969 | Kumin . | |
| 3,485,695 | 12/1969 | Ness | 156/229 |
| 3,575,784 | 4/1971 | Phillips et al. . | |
| 3,772,417 | 11/1973 | Vogt | 264/230 |
| 3,932,682 | 1/1976 | Loft et al. | 428/296 |
| 3,949,128 | 4/1976 | Ostermeier | 428/152 |
| 4,013,816 | 3/1977 | Sabee et al. | 428/288 |
| 4,041,203 | 8/1977 | Brock et al. | 428/157 |
| 4,048,364 | 9/1977 | Harding et al. | 428/113 |
| 4,193,899 | 3/1980 | Brenner et al. . | |
| 4,209,563 | 6/1980 | Sisson | 428/288 |
| 4,342,812 | 8/1982 | Selwood | 428/286 |
| 4,443,513 | 4/1984 | Meitner et al. | 422/195 |
| 4,467,595 | 8/1984 | Kramers | 57/225 |
| 4,486,485 | 12/1984 | Sookne | 428/198 |
| 4,489,543 | 12/1984 | Bromley et al. | 57/208 |
| 4,515,854 | 5/1985 | Kogame et al. | 428/288 |
| 4,551,378 | 11/1985 | Carey, Jr. | 428/198 |
| 4,554,121 | 11/1985 | Kramers | 264/103 |
| 4,554,207 | 11/1985 | Lee | 428/288 |
| 4,578,307 | 3/1986 | Niki et al. | 428/288 |
| 4,606,964 | 8/1986 | Wideman | 428/152 |
| 4,612,148 | 9/1986 | Motooka et al. | 264/49 |
| 4,652,487 | 3/1987 | Morman | 428/138 |
| 4,657,802 | 4/1987 | Morman | 428/152 |
| 4,696,779 | 9/1987 | Wideman | 264/211.13 |
| 4,714,647 | 12/1987 | Shipp, Jr. et al. | 428/212 |
| 4,720,415 | 1/1988 | VanderWielen et al. | 428/152 |
| 4,781,966 | 11/1988 | Taylor | 428/152 |
| 4,965,122 | 10/1990 | Morman | 428/225 |
| 5,244,482 | 9/1993 | Hassenboehler, Jr. et al. | 55/528 |

FOREIGN PATENT DOCUMENTS

| | | |
|---|---|---|
| 0019295 | 11/1980 | European Pat. Off. . |
| 0030418 | 6/1981 | European Pat. Off. . |
| 0127483 | 12/1984 | European Pat. Off. . |
| 0180703 | 3/1986 | European Pat. Off. . |
| 0184932 | 6/1986 | European Pat. Off. . |
| 0236091 | 9/1987 | European Pat. Off. . |
| 0237642 | 9/1987 | European Pat. Off. . |
| 0503590 | 9/1992 | European Pat. Off. . |
| 0503590A1 | 9/1992 | European Pat. Off. . |
| 0549954 | 7/1993 | European Pat. Off. ....... A41D 31/00 |
| 2205407 | 8/1982 | France . |
| 1460514 | 6/1978 | Germany . |
| 2046593 | 5/1980 | Germany . |
| 2613963 | 6/1985 | Germany . |
| 2757526 | 3/1986 | Germany . |
| 2632875 | 3/1986 | Germany . |
| 3438859 | 6/1989 | Germany . |
| 1217498 | 12/1970 | United Kingdom . |
| 1308904 | 3/1973 | United Kingdom . |
| 1399666 | 7/1975 | United Kingdom . |
| 1487488 | 9/1977 | United Kingdom . |
| 1532467 | 11/1978 | United Kingdom . |
| 1538671 | 1/1979 | United Kingdom . |
| 1576436 | 10/1980 | United Kingdom . |
| 1575972 | 10/1980 | United Kingdom . |
| 2149720 | 11/1984 | United Kingdom . |
| 2175026 | 4/1986 | United Kingdom . |

OTHER PUBLICATIONS

Translation of PCT/JP91/00594.

*Primary Examiner*—James C. Cannon
*Attorney, Agent, or Firm*—James B. Robinson; Karl V. Sidor

[57] ABSTRACT

Disclosed is a method of producing a barrier fabric having stretch and recovery properties. The method includes the steps of heating at least one nonwoven web containing meltblown non-elastic thermoplastic polymer fibers to a temperature at which the peak total energy absorbed by the nonwoven web of meltblown fibers is at least about 250 percent greater than the amount absorbed by the nonwoven web of meltblown fibers at room temperature; applying a tensioning force to neck the heated nonwoven web; and cooling the necked nonwoven web so that the nonwoven web has at least the same hydrostatic head and/or particulate barrier properties as the nonwoven web before necking. Also disclosed is a stretchable barrier fabric composed of a nonwoven web of meltblown non-elastomeric thermoplastic polymer fibers, the nonwoven web being heat treated so that it is adapted to stretch at least about 10 percent more than an identical untreated nonwoven web of meltblown non-elastomeric thermoplastic polymer fibers. The stretchable barrier fabric is adapted to provide a hydrostatic head of at least about 20 cm and/or a particle holdout efficiency of at least about 40 percent for particles having an average size greater than 0.1 micron. The stretchable barrier fabric may be a component of a multilayer material and may be used in disposable protective garments.

31 Claims, 13 Drawing Sheets

STRETCHABLE MELTBLOWN FABRIC WITH BARRIER PROPERTIES

This application is a continuation of application Ser. No. 07/990,161 entitled "Stretchable Meltblown Fabric with Barrier Properties" and filed in the U.S. Patent and Trademark Office on Dec. 14, 1992, now abandoned.

FIELD OF THE INVENTION

The present invention relates to materials having stretch and recovery properties and a method of making those materials.

BACKGROUND

There are many types of limited use or disposable protective apparel that are designed to provide barrier properties. Examples of such apparel include surgical gowns, patient drapes, face masks, shoe covers, industrial work wear and coveralls. Other examples include outer covers of disposable personal care products such as disposable diapers and incontinence garments.

For most applications, protective apparel needs to be made from fabrics that are relatively impervious to liquids and/or particulates. These barrier fabrics must also be suited for the manufacture of protective apparel at such low cost that the garments may be discarded after only a single use. Most inexpensive materials used for protective apparel have an important flaw. They are uncomfortable.

One such barrier fabric is a calendered flash-spun polyethylene spunbond fabric known as Tyvek®. This fabric is available from E. I. duPont De Nemours & Company. Although Tyvek® is inexpensive, it offers little breathability or stretch and so is uncomfortable to wear. Another type of material is generally known as spunlace fabric. E. I. DuPont De Nemours & Company provides a spunlace fabric under the trade designation Sontara®. Spunlace fabric generally refers to a material which has been subjected to hydraulic entangling. Although spunlace fabric is relatively inexpensive, breathable and can be deformed, the deformation is generally considered to be permanent and can be described as non-recoverable stretch. Nonwoven webs of very small diameter fibers or microfibers have long been known to be permeable to air and water vapor while remaining relatively impermeable to liquids and/or particulates. Useful webs of small diameter fibers can be made by extruding non-elastomeric thermoplastic polymers utilizing fiber forming processes such as, for example, meltblowing processes. Although nonwoven webs of meltblown fibers formed from non-elastomeric polymers are relatively inexpensive and breathable, those highly entangled webs tend to respond poorly to stretching forces. Elongation that occurs in such materials is generally considered to be a permanent, non-recoverable elongation (i.e., non-recoverable stretch). For example, nonwoven webs made from conventional thermoplastic polypropylene are usually considered to have non-recoverable stretch.

It is desirable to have a material that is permeable to air and water vapor yet is relatively impermeable to liquids and/or particulates. Such a "breathable" material can dramatically increase the comfort of someone wearing a garment, especially if the garment must be worn under high heat index conditions, during vigorous physical activity, or for very long periods. Ventilation holes, ports and/or panels may be relatively ineffective and can compromise the protection of the wearer. Furthermore, a process of manufacturing garments with ventilation holes, ports and/or panels generally tends to be more complex and less efficient than a process of making garments without such features. Complex and relatively inefficient manufacturing processes can eliminate the cost advantages provided by inexpensive materials.

With respect to stretch properties, materials which are readily stretchable and have recovery (i.e., materials that contract upon termination of a biasing force following stretching of the material by application of the biasing force) are generally considered to be more comfortable than materials having "non-recoverable stretch" (i.e., materials that do not contract upon termination of a biasing force). Stretch and recovery is desirable in situations where sudden movement could cause a garment made of an unyielding fabric to rip open. Also, stretch and recovery are desirable in situations where sagging fabric or very loose fitting, baggy garments may snag and tear or otherwise pose a hazard.

In the past, stretch and recovery have been imparted to garments by adding elastomeric sections, pieces and/or strips. These elastomeric components have included nonwoven webs made from elastomeric polymers. Although such elastomeric materials provide highly desirable stretch and recovery, they are relatively expensive when compared to non-woven materials made from non-elastomeric polymers such as, commodity polyolefins. Additionally, some elastomeric materials may degrade upon exposure to certain liquids and/or gases that can be present in many industrial and medical environments. Furthermore, a process of manufacturing garments by joining several different types of fabric together generally tends to be more complex and less efficient than a process of making garments from a single fabric. Complex and relatively inefficient manufacturing processes generally reduce the cost advantages provided by inexpensive materials.

One material that has demonstrated stretch without requiring elastomeric materials has been suggested in U.S. Pat. No. 4,965,122. According to that patent, a tensioning force is applied to a fabric to reduce its width while the fabric is at ambient temperature. The material is then heated and cooled while it is necked so that it retains a memory of its necked condition which causes it to recover to generally about its necked dimensions after non-destructive stretching in the necked directed. While such a process works well with certain materials, it is largely unacceptable for treating a nonwoven web of very fine fibers such as meltblown microfibers, especially when it is important to preserve the barrier properties of the web. Generally speaking, nonwoven webs of non-elastic meltblown microfibers suitable as barrier materials have a highly entangled network of fibers. Instead of necking, such webs tend to tear or rip when any appreciable tensioning force is applied at room temperature.

Thus, a need exists for an inexpensive material which is permeable to air and water vapor yet relatively impermeable to liquids and/or particulates and which has stretch and recovery properties. There is also a need for a material having those properties which is relatively tough, durable, conformable, lightweight and suited for high-speed manufacturing and converting processes. There is a need for apparel/garments that are relatively impermeable to liquids and/or particulates and require little or no other materials, components, treatments, or the like to provide desirable comfort features such as, for example, conformability, breathability, and stretch and recovery properties. For example, a need exists for protective garments that are composed substantially or entirely of an inexpensive material such that the garments are relatively impermeable to liquids and/or particulates and so inexpensive as to be disposable while also being conformable, breathable, and having stretch and recovery properties.

DEFINITIONS

As used herein, the terms "stretch" and "elongation" refer to the difference between the initial dimension of a material and that same dimension after the material is stretched or extended following the application of a biasing force. Percent stretch or elongation may be expressed as [(stretched length—initial sample length) /initial sample length] ×100. For example, if a material having an initial length of 1 inch is stretched 0.85 inch, that is, to a stretched or extended length of 1.85 inches, that material can be said to have a stretch of 85 percent.

As used herein, the term "recovery" refers to the contraction of a stretched or elongated material upon termination of a biasing force following stretching of the material from some initial measurement by application of the biasing force. For example, if a material having a relaxed, unbiased length of one (1) inch is elongated 50 percent by stretching to a length of one-and-one-half (1.5) inches, the material is elongated 50 percent (0.5 inch) and has a stretched length that is 150 percent of its relaxed length. If this stretched material contracts, that is, recovers to a length of one-and-one-tenth (1.1) inches after release of the biasing and stretching force, the material has recovered 80 percent (0.4 inch) of its one-half (0.5) inch elongation. Percent recovery may be expressed as [(maximum stretch length—final sample length) / (maximum stretch length—initial sample length)]×100.

As used herein, the term "non-recoverable stretch" refers to elongation of a material upon application of a biasing force which is not followed by a contraction of the material as described above for "recovery". Non-recoverable stretch may be expressed as a percentage as follows:

Non-recoverable stretch=100–recovery when the recovery is expressed in percent.

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding and bonded carded web processes.

As used herein, the term "spunbonded web" refers to a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, the term "meltblown fibers" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, the term "microfibers" means small diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. patent application Ser. No. 07/779,929, entitled "A Nonwoven Web With Improved Barrier Properties" filed Nov. 26, 1991, and now abandoned incorporated herein by reference in its entirety.

As used herein, the term "thermoplastic material" refers to a high polymer that softens when exposed to heat and returns to its original condition when cooled to room temperature. Natural substances which exhibit this behavior are crude rubber and a number of waxes. Other exemplary thermoplastic materials include, without limitation, polyvinyl chloride, polyesters, nylons, polyfluorocarbons, polyethylene, polyurethane, polystyrene, polypropylene, polyvinyl alcohol, caprolactams, and cellulosic and acrylic resins.

As used herein, the term "disposable" is not limited to single use articles but also refers to articles that can be discarded if they become soiled or otherwise unusable after only a few uses.

As used herein, the term "garment" refers to protective apparel and/or shields including for example, but not limited to, surgical gowns, patient drapes, face masks, shoe covers, coveralls, work suits, aprons as well as outer covers for diapers, training pants and the like.

As used herein, the term "barrier fabric" refers to a fabric having a useful level of resistance to penetration by liquid and/or particulates. Generally speaking, resistance to liquid penetration is measured by hydrostatic head tests, strike-through tests, water spray penetration tests and the like. Resistance to penetration by particulates may be measured by determining the air filter retention of dry particles and can be expressed as a particles holdout efficiency. Generally speaking, barrier fabrics should resist penetration by a column of tap water of at least about 20 cm and/or should have a particle holdout efficiency of at least about 40 percent for particles having a diameter greater than about 0.1 micron.

As used herein, the term "hydrostatic head" refers to a material's resistance to water penetration as determined in accordance with the standard hydrostatic pressure test AATCCTM No. 127–1977 with the following exceptions: (1) The samples are larger than usual and are mounted in a stretching frame that clamps onto the cross-machine direction ends of the sample, such that the samples may be tested under a variety of stretch conditions (e.g., 10%, 20%, 30%, 40% stretch); and (2) The samples are supported underneath by a plastic mesh or net having a hexagonal pattern of about 64 hexagons per square inch to prevent the sample from sagging under the weight of the column of water.

As used herein, the term "particle hold-out efficiency" refers to the efficiency of a material at preventing the passage of particles of a certain size range through the material. A high particle holdout efficiency is desirable. Particle holdout efficiency may be measured by determining the air filter retention of dry particles utilizing tests such as, for example, IBR Test Method No. E-217, Revision G (1/15/91) performed by InterBasic Resources, Inc. of Grass Lake, Mich. Generally speaking, in such tests particulate matter is dispersed into the air on the "challenge" side of a test fabric by means of a fan which directs the particle-containing air onto the face of the test fabric. The concentration of dust particles in the "challenge" atmosphere and the concentration of dust particles in the atmosphere on the reverse side of the test fabric (i.e., the particles that have passed through the fabric) are measured in various size ranges by a particle counter. A particle holdout efficiency is calculated from the difference in the concentration.

The term "$\alpha$-transition" as used herein refers a phenomenon that occurs in generally crystalline thermoplastic polymers. The $\alpha$-transition denotes the highest temperature transition below the melt transition ($T_m$) and is often referred to as pre-melting. Below the $\alpha$-transition, crystals in a polymer are fixed. Above the $\alpha$-transition, crystals can be annealed into modified structures. The $\alpha$-transition is well known and has been described in such publications as, for example, Mechanical Properties of Polymers and Composites (Vol. 1) by Lawrence E. Nielsen; and Polymer Monographs, ed. H. Morawetz, (Vol. 2-Polypropylene by H. P. Frank). Generally speaking, the $\alpha$-transition is determined using Differential Scanning Calorimetry techniques on equipment such as, for example, a Mettler DSC 30 Differential Scanning Calorimeter. Standard conditions for typical measurements are as follows: Heat profile, 30° C. to a temperature about 30° C. above the polymer melt point at a rate of 10° C./minute; Atmosphere, Nitrogen at 60 SCC/minute; Sample size, 3 to 5 milligrams.

The expression "onset of melting at a liquid fraction of five percent" refers to a temperature which corresponds to a specified magnitude of phase change in a generally crystalline polymer near its melt transition. The onset of melting occurs at a temperature which is lower than the melt transition and is characterized by different ratios of liquid fraction to solid fraction in the polymer. The onset of melting is determined using Differential Scanning Calorimetry techniques on equipment such as, for example, a Mettler DSC 30 Differential Scanning Calorimeter. Standard conditions for typical measurements are as follows: Heat profile, 30° to a temperature about 30° C. above the polymer melt point at a rate of 10° C./minute; Atmosphere, Nitrogen at 60 SCC/minute; Sample size, 3 to 5 milligrams.

As used herein, the term "necked material" refers to any material which has been constricted in at least one dimension by processes such as, for example, drawing.

As used herein, the term "neckable material" means any material which can be necked.

As used herein, the term "stretch direction" refers to the direction of stretch and recovery.

As used herein, the term "percent neck-down" refers to the ratio determined by measuring the difference between the pre-necked dimension and the necked dimension of a neckable material and then dividing that difference by the pre-necked dimension of the neckable material; this quantity multiplied by 100. For example, the percent neck-down may be represented by the following expression: percent neck-down =[(pre-necked dimension-necked dimension)/pre-necked dimension]×100

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates or materials added to enhance processability of a composition.

SUMMARY OF THE INVENTION

The present invention addresses the above described needs by providing a method of treating a nonwoven barrier fabric containing non-elastomeric meltblown thermoplastic polymer fibers so that the nonwoven barrier fabric has stretch and recovery properties. Generally speaking, the method of the present invention includes the steps of (1) heating a nonwoven barrier fabric containing meltblown nonelastic thermoplastic polymer fibers to a temperature at which the peak total energy absorbed by the web is at least about 250 percent greater than the amount absorbed by the web at room temperature; (2) applying a tensioning force to neck the heated nonwoven fabric; and (3) cooling the necked nonwoven fabric, so that the necked nonwoven fabric has stretch and recovery properties as well as useful levels of resistance to penetration by liquids and/or particulates. For example, the stretchable barrier fabric should have at least the same hydrostatic head and/or particulate barrier properties as the barrier fabric before the heat treatment and necking.

According to the invention, the nonwoven barrier fabric containing meltblown non-elastic thermoplastic polymer fibers can be heated to a temperature at which the peak total energy absorbed by the web is at least about 275 percent greater than the amount absorbed by the web at room temperature. For example, the web can be heated to a temperature at which the peak total energy absorbed by the web is from about 300 percent greater to more than about 1000 percent greater than the amount absorbed by the web at room temperature.

A barrier fabric having stretch and recovery properties imparted by the above described treatment can be characterized as having a hydrostatic head of at least about 20 cm and the ability to stretch at least about 10 percent more than an identical untreated barrier fabric. For example, the stretchable meltblown fiber barrier fabric may have a hydrostatic head of at least about 30 cm and may be adapted to stretch from about 15 to about 300 percent more than an identical untreated barrier fabric. As a further example, the stretchable meltblown fiber barrier fabric may have a hydrostatic head of from about 35 cm to about 120 cm and may be adapted to stretch from about 20 to about 200 percent more than an identical untreated barrier fabric. As yet another example, the stretchable meltblown fiber barrier fabric may have a hydrostatic head of from about 40 cm to about 90 cm.

In one aspect of the present invention, the stretchable meltblown fiber barrier fabric may be adapted to stretch from about 15 percent to about 100 percent. For example, from about 20 to about 80 percent. The stretchable meltblown fiber barrier fabric may be adapted recover at least about 50 percent when stretched 60 percent. For example, the stretchable meltblown fiber barrier fabric may be adapted to stretch from about 15 percent to about 60 percent and recover at least about 90 percent when stretched an amount between from about 15 percent to about 60 percent.

According to another aspect of the present invention, the stretchable barrier fabric may have a porosity exceeding about 30 (ft$^3$/min)/ft$^2$ (also, CFM/ft$^2$). For example, the barrier fabric may have a porosity ranging from about 35 to about 70 CFM/ft$^2$. The barrier fabric may have a basis weight of from about 6 to about 400 grams per square meter (gsm). For example, the basis weight may range from about 20 to about 150 grams per square meter.

The meltblown fibers of the stretchable barrier fabric may include meltblown microfibers. Desirably, at least about 50 percent, as determined by optical image analysis, of the meltblown microfibers will have an average diameter of less than 5 microns. For example, at least about 50 percent of the meltblown fibers may be ultra-fine microfibers having an average diameter about 3 microns or less. As a further example, from about 60 percent to about 100 percent of the meltblown microfibers may have an average diameter of less than 5 microns or may be ultrafine microfibers. The meltblown fibers are formed from a non-elastomeric thermoplastic polymer which may be, for example, a polyolefin, polyester, or polyamide. If the polymer is a polyolefin, it may be polyethylene, polypropylene, polybutene, ethylene copolymers, propylene copolymers, butene copolymers and/or blends of the above. The nonwoven web may also be a mixture of meltblown fibers and one or more secondary materials such as, for example, textile fibers, wood pulp fibers, particulates and super-absorbent materials. Where the meltblown fibers are formed from a polyolefin, the above-described heat treatment typically takes place at a temperature ranging from greater than the polymer's α-transition to about 10 percent below the onset of melting at a liquid fraction of 5 percent In one aspect of the present invention, one or more layers of the meltblown fiber barrier fabric having stretch and recovery properties may be joined with one or more other layers of material to form a multi-layer laminate. The other layers may be, for example, woven fabrics, knit fabrics, bonded carded webs, continuous filament webs (e.g., spun-bonded webs), meltblown fiber webs, and combinations thereof.

In another aspect of the present invention, there is provided a disposable protective garment composed of generally planar sections joined by seams, in which at least one of the generally planar sections is a material composed of at least one layer of the stretchable barrier fabric described above. The seams may be, for example, conventional stitched seams or seams provided by ultrasonic welding, solvent welding, thermal welding or the like.

The disposable protective garment may have a body portion, sleeve portions and leg portions extending therefrom. For example, the disposable protective garment may be a protective suit which includes: (1) a top section having a body portion and sleeve portions extending therefrom, and (2) a bottom section having leg portions. Desirably, the stretch direction of the stretchable barrier fabric will be generally parallel to the direction of motion of one or more of the body portion, sleeve portions or leg portions. In another aspect of the present invention, the disposable protective garment may be a gown having a body portion and sleeve portions extending therefrom. Desirably, the stretch direction of the stretchable barrier fabric will be generally parallel to the direction of motion of one or more of the body portion and sleeve portions.

DETAILED DESCRIPTION

Figure 1:
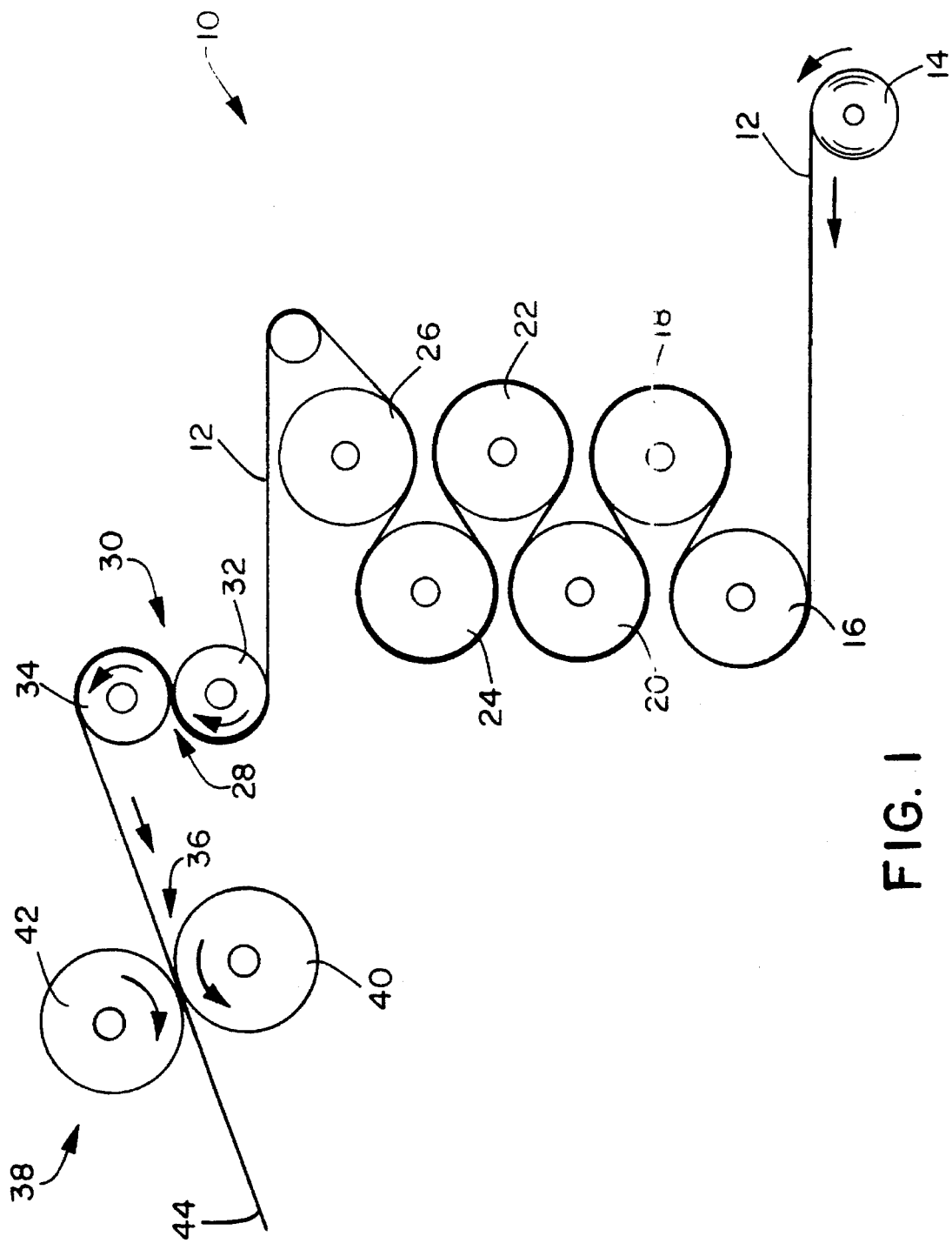
FIG. 1 is a schematic representation of an exemplary process for forming a stretchable barrier fabric utilizing a series of steam cans.

Referring to FIG. 1 of the drawings there is schematically illustrated at 10 an exemplary process for making a barrier fabric having stretch and recovery properties. FIG. 1 depicts a process in which the heat treatment is carried out utilizing a series of heated drums.

According to the present invention, a nonwoven neckable material 12 is unwound from a supply roll 14 and travels in the direction indicated by the arrow associated therewith as the supply roll 14 rotates in the direction of the arrows associated therewith.

The nonwoven neckable material 12 may be formed by one or more meltblowing processes and passed directly through the nip 16 without first being stored on a supply roll 14.

The neckable material 12 passes over a series of heated drums (e.g., steam cans) 16–26 in a series of reverse S-loops. The steam cans 16–26 typically have an outside diameter of about 24 inches although other sized cans may be used. The contact time or residence time of the neckable material on the steam cans to effect heat treatment will vary depending on factors such as, for example, steam can temperature, type and/or basis weight of material, and diameter of the meltblown fibers in the material. The contact time should be sufficient to heat the nonwoven neckable material 12 to a temperature at which the peak total energy absorbed by the neckable material is at least about 250 percent greater than the amount absorbed by the neckable material 12 at room temperature. For example, the contact time should be sufficient to heat the nonwoven neckable material 12 to a temperature at which the peak total energy absorbed by the neckable material is at least about 275 percent greater than the amount absorbed by the neckable material at room temperature. As a further example, the neckable material can be heated to a temperature at which the peak total energy absorbed by the neckable material is from about 300 percent greater to more than about 1000 percent greater than the amount absorbed by the neckable material at room temperature.

Generally speaking, when the nonwoven neckable material 12 is a nonwoven web of meltblown thermoplastic polymer fibers formed from a polyolefin such as, for example, polypropylene, the residence time on the steam cans should be sufficient to heat the meltblown fibers to a temperature ranging from greater than the polymer's α-transition to about 10 percent below the onset of melting at a liquid fraction of 5 percent.

For example, a nonwoven web of meltblown polypropylene fibers may be passed over a series of steam cans heated to a measured surface temperature from about 90° to about 150° C. (194°–302° F.) for a contact time of about 1 to about 300 seconds to provide the desired heating of the web. Alternatively and/or additionally, the nonwoven web may be heated by infra-red radiation, microwaves, ultrasonic energy, flame, hot gases, hot liquids and the like. For example, the nonwoven web may be passed through a hot oven.

Although the inventors should not be held to a particular theory, it is believed that heating a nonwoven web of meltblown thermoplastic non-elastomeric, generally crystalline polymer fibers to a temperature greater than the polymer's α-transition before applying tension is important. Above the α-transition, crystals in the polymer fibers can be annealed into modified structures which, upon cooling in fibers held in a tensioned configuration, enhance the stretch and recovery properties (e.g., recovery from application of a stretching force) of a nonwoven web composed of such fibers. It is also believed that the meltblown fibers should not be heated to a temperature greater than the constituent polymer's onset of melting at a liquid fraction of five percent. Desirably, this temperature should be more than 10 percent below the temperature determined for the polymer's onset of melting at a liquid fraction of 5 percent. One way to roughly estimate a temperature approaching the upper limit of heating is to multiply the polymer melt temperature (expressed in degrees Kelvin) by 0.95.

Importantly, it is believed that heating the meltblown fibers within the specified temperature range permits the fibers to become bent, extended and/or drawn during necking rather than merely slipping over one another in response to the tensioning force.

The present invention may be practiced utilizing polymers such as, for example, polyolefins, polyesters and polyamides. Exemplary polyolefins include one or more of polyethylene, polypropylene, polybutene, ethylene copolymers, propylene copolymers and butene copolymers. Polypropylenes that have been found useful include, for example, polypropylene available from the Himont Corporation under the trade designation PF-015 and polypropylene available from the Exxon Chemical Company under the trade designation Exxon 3445G. Chemical characteristics of these materials are available from their respective manufacturers.

The nonwoven web of meltblown fibers may be formed utilizing conventional meltblowing processes. Desirably, the meltblown fibers of the nonwoven web will include meltblown microfibers to provide enhanced barrier properties. For example, at least about 50 percent, as determined by optical image analysis, of the meltblown microfibers may have an average diameter of less than about 5 microns. As yet another example, at least about 50 percent of the meltblown fibers may be ultra-fine microfibers that may have an average diameter of less than about 3 microns. As a further example, from about 60 percent to about 100 percent of the meltblown microfibers may have an average diameter of less than 5 microns or may be ultra-fine microfibers.

The nonwoven web may also be a mixture of meltblown fibers and one or more secondary materials. As an example of such a nonwoven web, reference is made to U.S. Pat. Nos. 4,100,324 and 4,803,117, the contents of each of which are incorporated herein by reference in their entirety, in which meltblown fibers and other materials are commingled to form a single coherent web of randomly dispersed fibers. Such mixtures may be formed by adding fibers and/or particulates to the gas stream in which meltblown fibers are carried so that an intimate entangled commingling of the meltblown fibers and other materials occurs prior to collection of the meltblown fibers upon a collection device to form a coherent web of randomly dispersed meltblown fibers and other materials. Useful materials which may be used in such nonwoven composite webs include, for example, wood pulp fibers, staple length fibers from natural and synthetic sources (e.g., cotton, wool, asbestos, rayon, polyester, polyamide, glass, polyolefin, cellulose derivatives and the like), multi-component fibers, absorbent fibers, electrically conductive fibers, and particulates such as, for example, activated charcoal/carbon, clays, starches, metal oxides, super-absorbent materials and mixtures of such materials. Other types of nonwoven composite webs may be used. For example, a hydraulically entangled nonwoven composite web may be used such as disclosed in U.S. Pat. Nos. 4,931,355 and 4,950,531 both to Radwanski, et al., the contents of which are incorporated herein by reference in their entirety.

From the steam cans, the heated neckable material 12 passes through the nip 28 of an S-roll arrangement 30 in a reverse-S path as indicated by the rotation direction arrows associated with the stack rollers 32 and 34. From the S-roll arrangement 30, the heated neckable material 12 passes through the nip 36 of a drive roller arrangement 38 formed by the drive rollers 40 and 42. Because the peripheral linear speed of the rollers of the S-roll arrangement 30 is controlled to be less than the peripheral linear speed of the rollers of the drive roller arrangement 38, the heated neckable material 12 is tensioned between the S-roll arrangement 30 and the nip of the drive roll arrangement 38. By adjusting the difference in the speeds of the rollers, the heated neckable material 12 is tensioned so that it necks a desired amount and is maintained in such tensioned, necked condition while it is cooled. Other factors affecting the neck-down of the heated neckable material are the distance between the rollers applying the tension, the number of drawing stages, and the total length of heated material that is maintained under tension. Cooling may be enhanced by the use of a cooling fluid such as, for example, chilled air or a water spray.

Generally speaking, the difference in the speeds of the rollers is sufficient to cause the heated neckable material 12 to neck-down to a width that is at least about 10 percent less than its original width (i.e., before application of the tensioning force). For example, the heated neckable material 12 may be necked-down to a width that is from about 15 percent to about 50 percent less than its original width.

The present invention contemplates using other methods of tensioning the heated neckable material 12. For example, tenter frames or other cross-machine direction stretcher arrangements that expand the neckable material 12 in other directions such as, for example, the cross-machine direction so that, upon cooling, the resulting material 44 will have stretch and recovery properties in a direction generally parallel to the direction that the material is necked.

An important feature of the present invention is that stretch and recovery is imparted to the barrier fabric of meltblown fibers and/or meltblown microfibers without compromising the barrier properties of the fabric. Meltblown fiber webs tend to resist necking because of their highly entangled fine fiber network. It is this same highly entangled network that is permeable to air and water vapor and yet is relatively impermeable to liquids and/or particulates. Gross changes in this fiber network such as rips or tears would permit penetration by liquids and/or particulates. Unfortunately, because they are relatively unyielding and resist necking, highly entangled networks of non-elastic meltblown fibers respond poorly to stretching forces and tend to rip or tear.

However, by heating the meltblown fiber web as described above, necking the heated material and then cooling it, a useful level of stretch and recovery can be imparted without sacrificing the desirable barrier properties of the meltblown fiber web. Generally speaking, the process of the present invention does not create rips or tears which would reduce the hydrostatic head or greatly increase the porosity of the barrier fabric. Measurement of the pore size distribution within the entangled fiber structure of the fabric before and after the process typically shows no significant changes. Attempts to produce barrier fabrics with high levels of stretch and recovery in the absence of heat have typically been unsuccessful. As shown in the Example section, nonwoven webs of meltblown fibers saturated with mineral oil, polytetrafluoroethylene, or water to serve as a lubricant could be necked only as much as a control sample in the absence of heat. Those same materials and the control sample ripped without further necking when higher levels of tension were applied.

Thus, the stretchable barrier fabrics of the present invention provide barrier properties at least as great as the barrier fabric did prior to processing. Desirably, the barrier fabrics of the present invention combine a hydrostatic head of at least about 20 cm with an ability to stretch at least about 10 percent and recover at least about 50 percent when stretched 10 percent. For example, the barrier fabrics of the present invention web may have a hydrostatic head of at least about 25 cm as well as the ability to stretch from about 15 percent to about 60 percent and recover at least about 50 percent when stretched 60 percent. Alternatively and/or additionally, the barrier fabrics of the present invention provide at least the above-described levels of stretch and recovery properties in combination with resistance to penetration by particulates expressed as a particle holdout efficiency of at least about 96 percent for particles having an average diameter ranging from about 1.5 microns to greater than about 10 microns. For example, the stretchable barrier fabric may have a particle holdout efficiency of about 98 percent for particles having an average diameter ranging from about 1.5 microns to about 7 microns. The stretchable barrier fabric may also have a particle holdout efficiency of at least about 40 percent for particles having an average diameter greater than about 0.1 micron. For example, the barrier fabric may have a particle holdout efficiency of at least about 40 percent for particles having an average diameter ranging from about 0.09 to about 1 micron. As a further example, the stretchable barrier fabric may have a particle holdout efficiency of about 50 percent or more for particles having an average diameter greater than about 0.1 micron. For example, the stretchable barrier fabric may have a particle holdout efficiency of about 50 percent or more for particles having an average diameter ranging from about 0.3 to about 1 micron.

Furthermore, the barrier fabric of the present invention may have a porosity exceeding about 15 ft$^3$/min/ft$^2$ (CFM/ft$^2$). For example, the barrier fabric may have a porosity ranging from about 30 to about 100 CFM/ft$^2$. As another example, the barrier fabric may have a porosity ranging from about 45 to about 90 CFM/ft$^2$.

Desirably, the barrier fabric has a basis weight of from about 6 to about 400 grams per square meter. For example, the basis weight may range from about 10 to about 150 grams per square meter. As another example, the basis weight may range from about 20 to about 90 grams per square meter. Barrier properties generally improve with increasing basis weight. In the past, heavier basis weights were needed to provide satisfactory levels of toughness and stretch before break while maintaining adequate barrier properties. The barrier fabric of the present invention provides satisfactory barrier at relatively low basis weights (e.g., about 10 gsm to about 30 gsm). This is due in part to the flexibility and pliability of the fabric which reduces the likelihood of tears and rips common to lightweight barrier materials and which destroy barrier properties. Thus, the present invention provides an economical and efficient barrier fabric for yet another reason in that it allows lightweight nonwoven barrier fabrics to be used more effectively.

The barrier fabric of the present invention may also be joined to one or more layers of another material to form a multi-layer laminate. The other layers may be, for example, woven fabrics, knit fabrics, bonded carded webs, continuous filaments webs, meltblown fiber webs, and combinations thereof. Desirably, the other materials will have about the same degree of stretch and recovery properties as the stretchable barrier fabric. For example, if the barrier fabric can be stretched up to about 25 percent and will recover about 85 percent when stretched 25 percent, the other layers of material should also be adapted to stretch up to about 25 percent.

Figure 3:
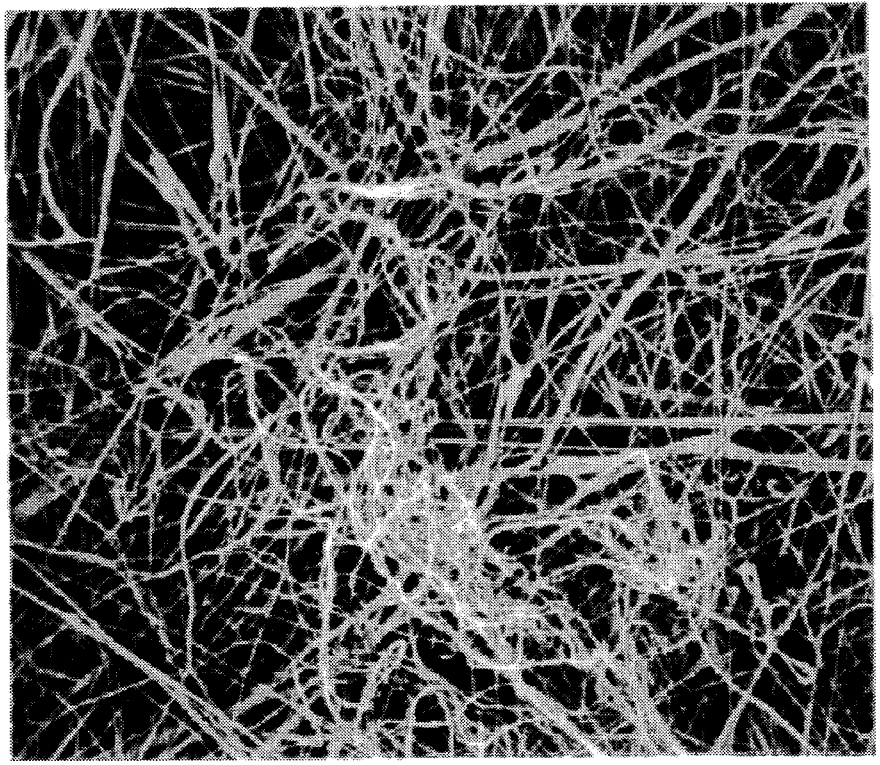
FIGS. 2 and 3 are photomicrographs of an exemplary neckable material, prior to treatment.
Figure 2:
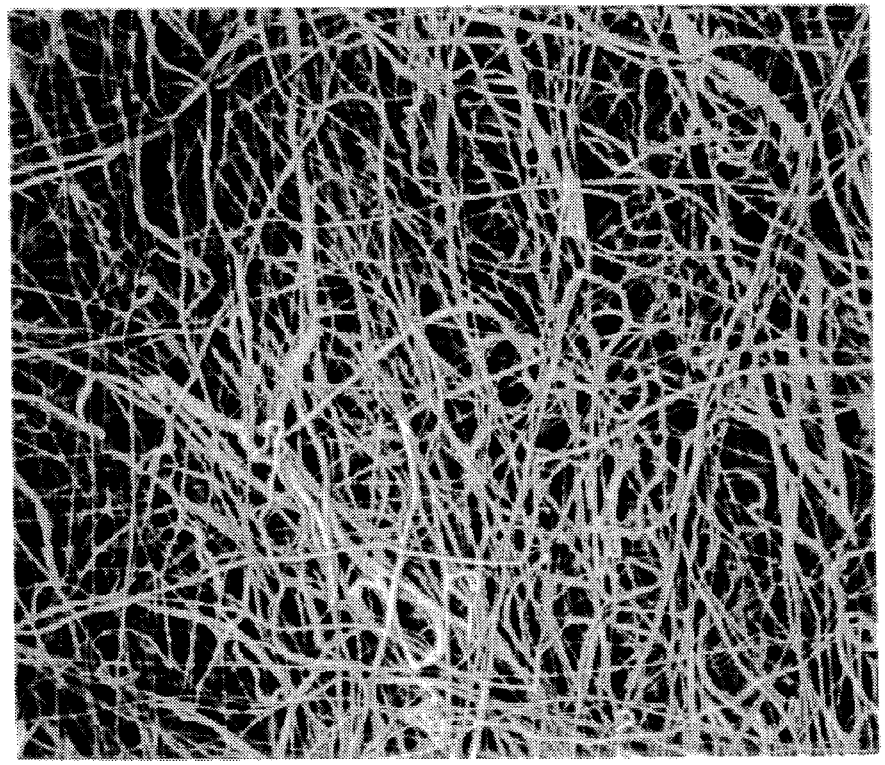

FIGS. 2–9 are scanning electron microphotographs of nonwoven webs of meltblown polypropylene fibers which have not been treated in accordance with the present invention. The fabrics shown in FIGS. 2 and 3 are 51 gsm nonwoven webs of meltblown polypropylene fibers formed utilizing conventional meltblowing process equipment.

Figure 5:
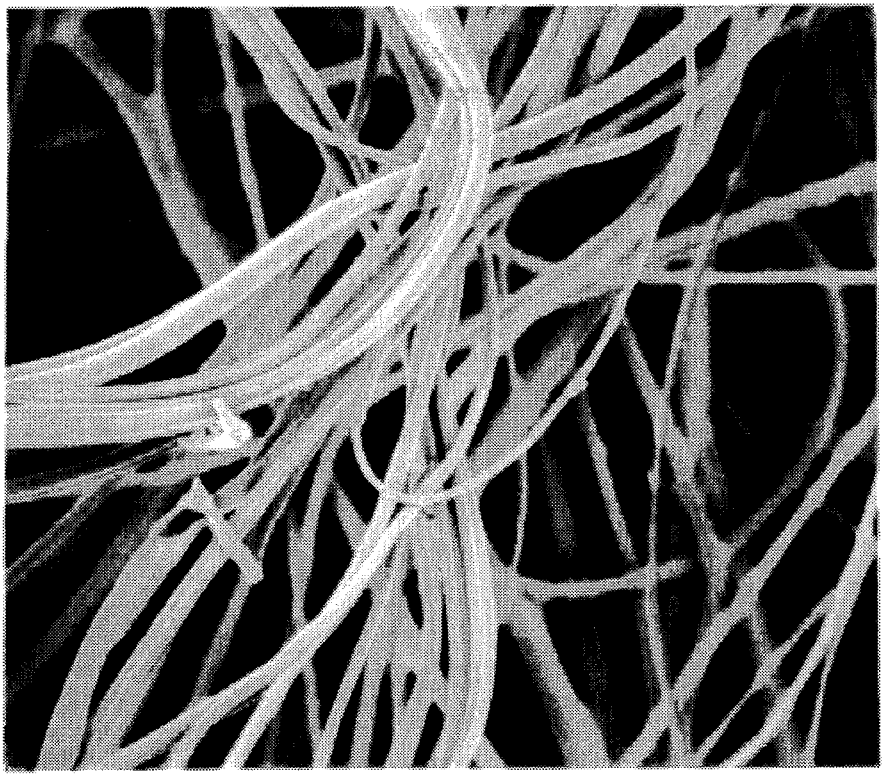
FIGS. 4, 5, 6, 7, 8 and 9 are enlarged photomicrographs of an exemplary neckable material, prior to treatment.
Figure 4:
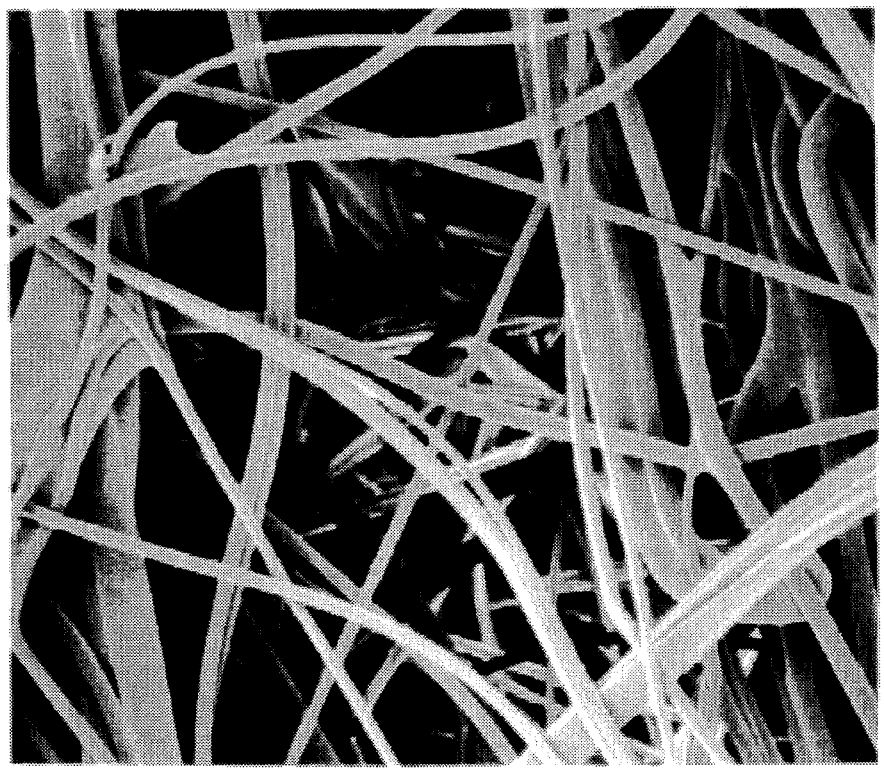
Figure 7:
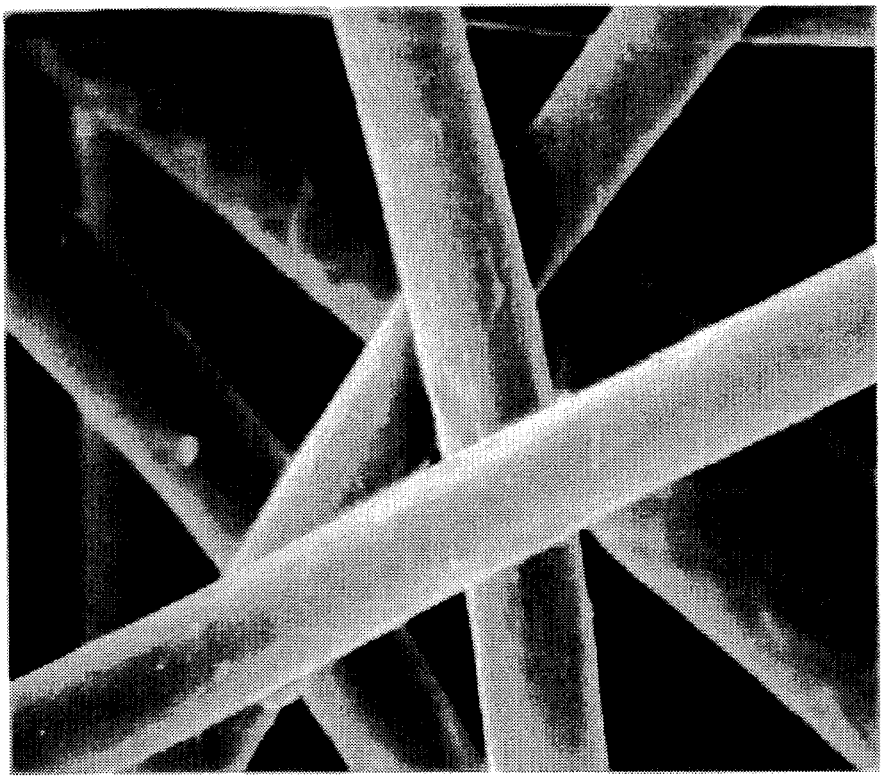
Figure 6:
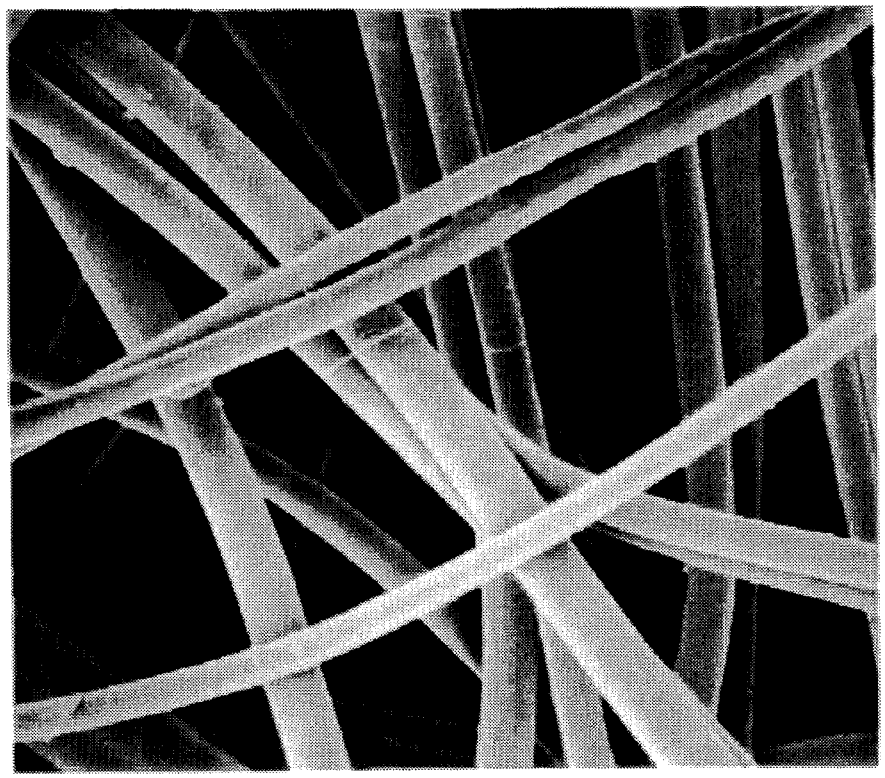
Figure 9:
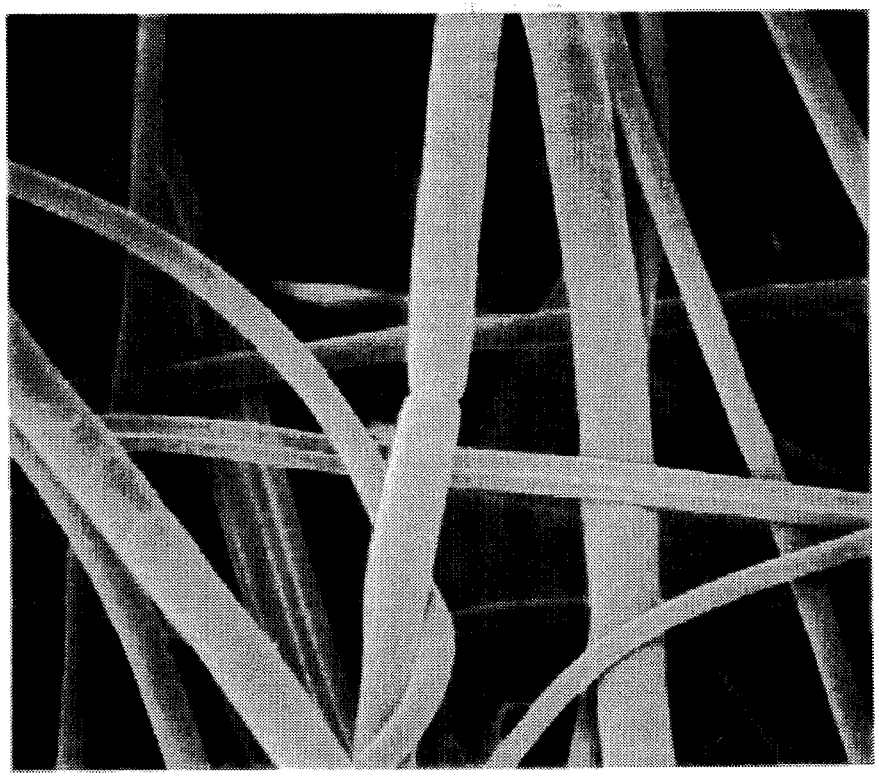
Figure 8:
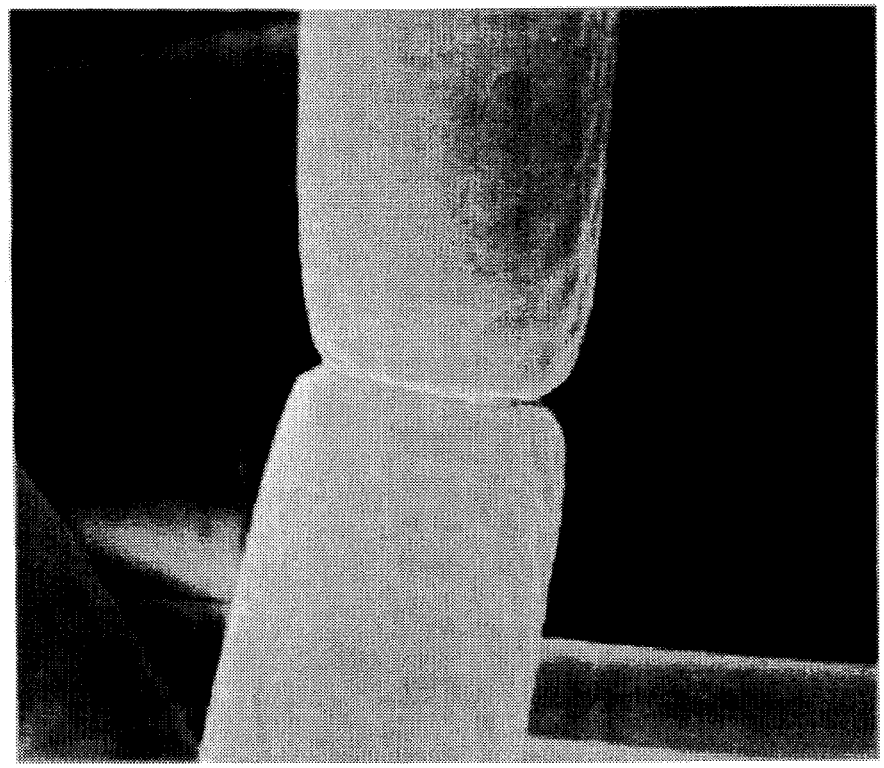

More particularly, FIGS. 2 and 3 are 50× (linear magnification) microphotographs of a nonwoven web of meltblown polypropylene fibers. FIGS. 4 and 5 are 500× (linear magnification) microphotographs of a portion of the material shown in FIGS. 2 and 3. FIG. 6 is a 1500× (linear magnification) microphotograph of a nonwoven web of meltblown polypropylene fibers. FIG. 7 is a 5000× (linear magnification) microphotograph of a nonwoven web of meltblown polypropylene fibers. FIG. 8 is a 5000× (linear magnification) microphotograph of a nonwoven web of meltblown polypropylene fibers. FIG. 9 is a 1000× (linear magnification) microphotograph of a nonwoven web of meltblown polypropylene fibers.

FIGS. 10–17 are scanning electron microphotographs of an exemplary stretchable barrier fabric of the present invention. The fabric shown in FIGS. 10–17 was made from 51 gsm nonwoven web of meltblown polypropylene fibers formed utilizing conventional meltblowing process equipment. Stretch and recovery properties were imparted to the nonwoven web of meltblown polypropylene fibers without diminishing its barrier properties by passing the web over a series of steam cans to the nonwoven web to a temperature of about 110° Centigrade for a total contact time of about 10 seconds; applying a tensioning force to neck the heated nonwoven web about 30 percent (i.e., a neck-down of about 30 percent); and cooling the necked nonwoven web.

Figure 11:
FIGS. 10 and 11 are photomicrographs of an exemplary stretchable barrier material.
Figure 10:

More particularly, FIGS. 10 and 11 are 50× (linear magnification) microphotographs of a stretchable barrier fabric composed of meltblown polypropylene fibers. When compared to FIGS. 2 and 3, the meltblown fibers of the stretchable barrier fabric have a much less random configuration and appear to be oriented across the width of the photograph.

Figure 13:
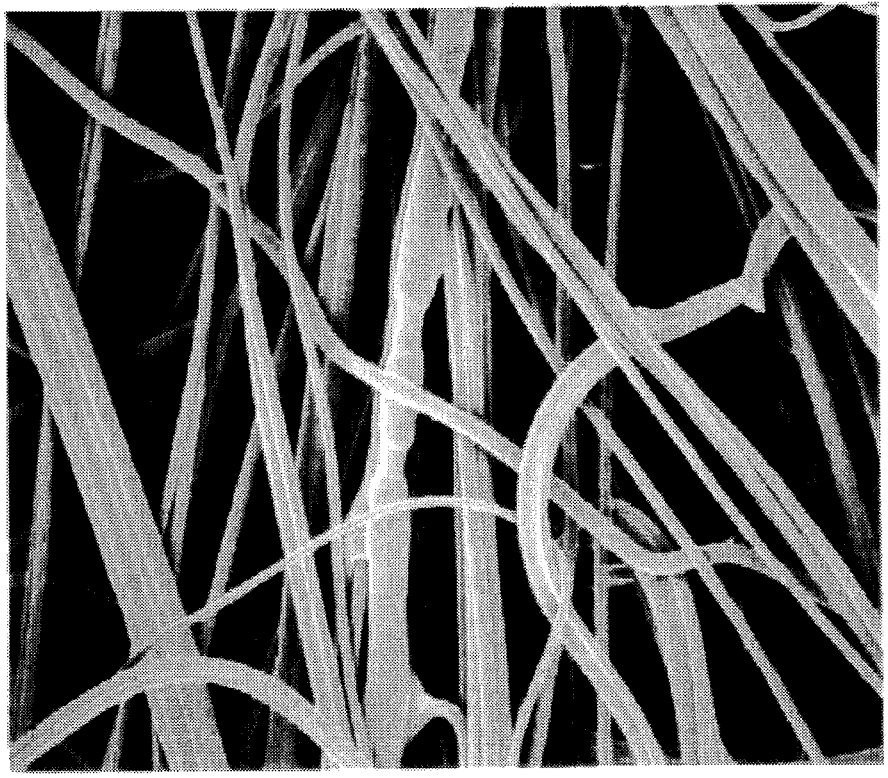
FIGS. 12, 13, 14, 15, 16 and 17 are enlarged photomicrographs of an exemplary stretchable barrier material.
Figure 12:
Figure 15:
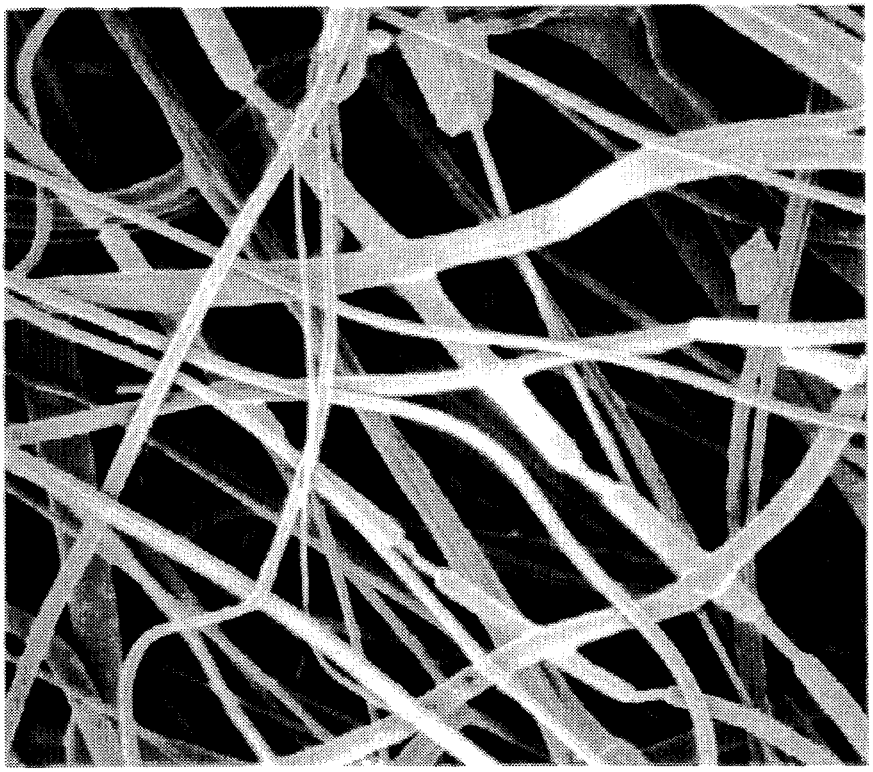
Figure 14:
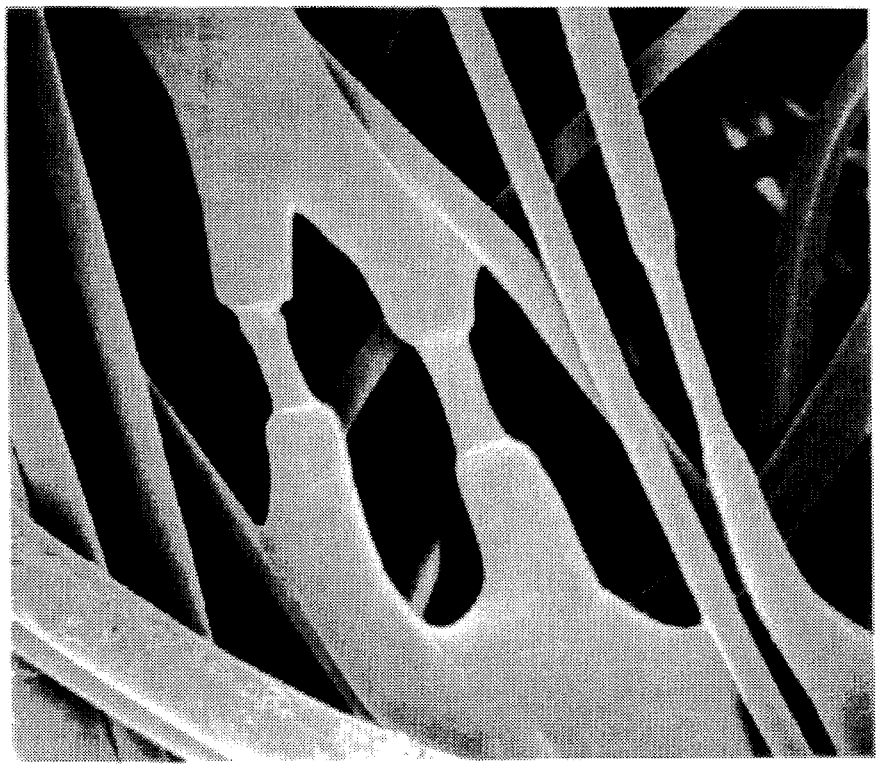
Figure 17:
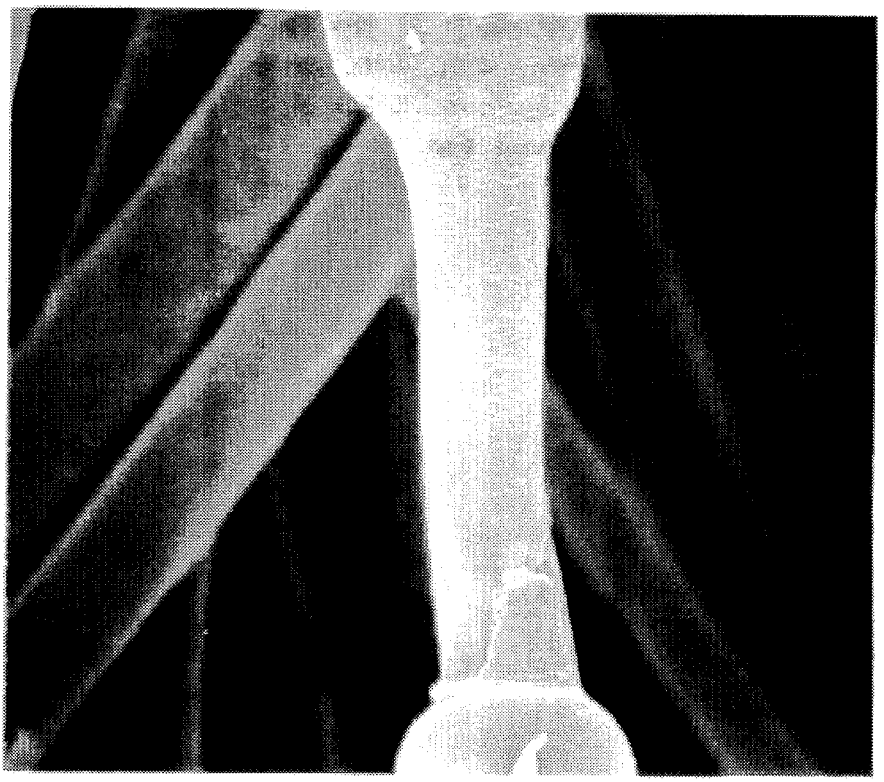
Figure 16:
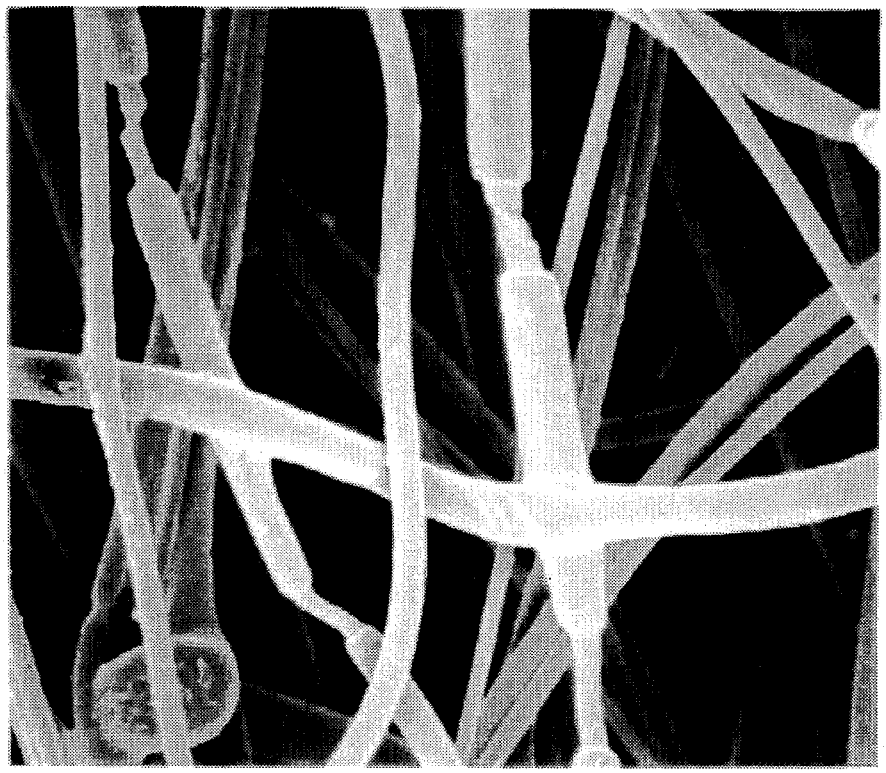

FIGS. 12 and 13 are 500× (linear magnification) microphotographs of a portion of the material shown in FIGS. 10 and 11. FIGS. 14–17 are microphotographs of different portions of the material shown in FIGS. 11 and 12. In particular, FIG. 14 is a 1500× (linear magnification) microphotograph of a barrier fabric having stretch and recovery properties. FIG. 15 is a 500× (linear magnification) microphotograph of a barrier fabric having stretch and recovery properties. FIG. 16 is a 1000× (linear magnification) microphotograph of a barrier fabric having stretch and recovery properties. FIG. 17 is a 5000× (linear magnification) microphotograph of a barrier fabric having stretch and recovery properties.

When compared to the meltblown polypropylene fibers shown in FIGS. 5–9, the meltblown polypropylene fibers shown in FIGS. 14–17 have small sections where the fiber diameter is less that the diameter of the surrounding portions. It appears that the meltblown polypropylene fibers have actually been drawn or extended while the tensioning force was applied to the heated fibers. Although the inventors should not be held to a particular theory of operation, it is believed that the presence of the drawn sections on the meltblown polypropylene fibers is an indication that the meltblown polypropylene fibers have been heated to a temperature ranging from greater than the polypropylene's α-transition to about 10 percent below the onset of melting at a liquid fraction of 5 percent and then stretched and cooled so that a nonwoven web of such fibers is adapted to have stretch and recovery properties.

EXAMPLE 1

A tensioning force was applied to neck a sample barrier fabric maintained under specific environmental conditions to see which, if any, conditions would yield appreciable amounts of necking. Breaks and/or tears at low levels of necking would indicate loss of barrier properties. All samples were tested on the same equipment in the same environmental chamber. The different conditions studied were:

1. "As is—RT" describes tests conducted at room temperature (about 70° F. or 21° C.) without any additives applied to the samples.
2. "As is–90° C." same as condition 1, except the samples were tested in an environmental chamber set at 90° C.
3. "As is–130° C." same as condition 1, except the samples were tested in an environmental chamber set at 130° C.
4. "Mineral oil—RT" describes tests conducted at room temperature on samples that were saturated with mineral oil and patted dry on paper toweling.
5. "Mineral oil–130° C." same as condition 4, except the samples were tested in an environmental chamber set to 130° C.
6. "Teflon® coated—RT" describes tests conducted at room temperature on samples that were treated with Scotchguard® as a source of polytetrofluroethylene.
7. "Water saturated—RT" describes tests conducted at room temperature on samples that were saturated with tap water containing a small amount of Aerosol OT 75 wetting agent.

Two types of nonwoven barrier fabrics were used: (1) a bonded nonwoven web of meltblown polypropylene fibers having a basis weight of about 34 grams per square meter (gsm), and (2) an unbonded nonwoven web of meltblown polypropylene fibers having a basis weight of about 51 gsm.

A sample measuring about 3 inch by 6 inches (6 inch length running parallel to the machine direction (MD) of the sample) was loaded into the 3 inch by 1 inch (i.e., each jaw was 3 inches wide by 1 inch high) jaws of an Instron Model 1122 Universal Test Instrument. The jaws were surrounded by an Instron Model 3111 series 808 environmental chamber (which had a window in the door) during the tests so the sample environment (temperature) could be controlled. The environmental chamber was preset to a desired temperature and allowed to come to equilibrium. A thermometer was used to insure an accurate temperature reading.

After loading the jaws, the sample was held in the chamber for at least three minutes to permit the sample to heat up and let the chamber reattain equilibrium.

A video camera was moved into position so the sample could be seen through a window in the chamber. The distance from the camera lens to the sample was about 12 inches. A macro lens was used and focused to enlarge the sample. The camera was started and run for about 5 seconds to provide a sample width reading at zero tension before the Instron crosshead was started. The following Instron measurements were made for each sample: (1) peak load, peak elongation, and peak total energy absorbed; and (2) break load, break elongation and total energy absorbed at break. The tensile testing was conducted utilizing the Instron test equipment essentially in accordance with Method 5100 of Federal Test Method Standard No. 191A. The sample gauge length was set at 3 inches and the cross-head speed was set at 12 inches per minute.

The video camera tape was replayed on a freeze frame tape player. The freeze frame feature was used so the sample width could be measured directly off the viewing screen. One measurement was made viewing the tape of the unstretched sample (i.e., before starting the Instron test equipment). The tape was advanced to the point at which the sample broke and then backed-up a couple of frames to the point just before the sample broke. A minimum sample width was measured directly off the viewing screen.

With respect to tensile properties, load refers to the force or resistance encountered while elongating a sample. Peak load refers to the maximum load encountered when elongating the sample. Break load refers the load encountered at the break or failure of a sample. As used herein, load is expressed in units of force (e.g., pounds$_{force}$) for samples measuring 3 inches wide by 6 inches long.

Total energy absorbed refers to the total area under a stress versus strain (i.e., load vs. elongation) curve up to a specified load. Peak total energy absorbed is the total area under such a curve up to the point of peak or maximum load. Total energy absorbed at break is the total area under such a curve up to the load at break or failure of the sample. Total energy absorbed is expressed in units of work/(length)$^2$ such as, for example, (inch ● lbs$_{force}$)/(inch)$^2$.

Elongation or stretch refers to a ratio determined by measuring the difference between a nonwoven web's initial unextended measurement (e.g., length) and its extended measurement in a particular dimension and dividing that difference by the nonwoven web's initial unextended measurement in that same dimension. This value is multiplied by 100 percent when elongation is expressed as a percent. Peak elongation is the elongation measured when the material has been stretched to its peak load. Break elongation is the elongation measured when the material has be stretched to break or failure.

The data from testing under the different conditions described above is presented on Tables 1–5. Table 1 provides the "neck-down" properties of the bonded material (i.e., the pattern bonded nonwoven web of meltblown propylene fibers—basis weight 34 gsm). Table 2 is a summary of the tensile data for the bonded material. Table 3 gives the neck-down properties of the unbonded materials (i.e., a nonwoven web of meltblown polypropylene fibers basis weight 51 gsm). Table 4 is a summary of the tensile data for the unbonded material. Table 5 provides a summary of the tensile properties for the unbonded material (i.e., a nonwoven web of meltblown polypropylene fibers—basis weight 51 gsm) measured during tests conducted at temperatures of 30° C., 55° C., 82° C., 95° C., 105° C., 130° C., and 150° C.

TABLE 1

MEASUREMENT OF SAMPLE WIDTH BEFORE TESTING AND AT BREAK

| SAMPLE | Initial Width (mm) | Break Width (mm) | Diff. (mm) | Percent Neck-down |
|---|---|---|---|---|
| MELTBLOWN: BONDED | | | | |
| AS IS - RT | 146 | 112 | 34 | 23.3 |
| AVG = 21.0 | 138 | 114 | 24 | 17.4 |
| STD* = 3.8 | 157 | 115 | 42 | 26.8 |
|  | 157 | 131 | 26 | 16.6 |
|  | 160 | 126 | 34 | 21.3 |
| AS IS 90° C. | 145 | 81 | 64 | 44.1 |
| AVG = 43.7 | 128 | 75 | 53 | 41.4 |
| STD = 2.1 | 152 | 80 | 72 | 47.4 |
|  | 159 | 92 | 67 | 42.1 |
|  | 154 | 87 | 67 | 43.5 |
| AS IS 130° C. | 153 | 84 | 69 | 45.1 |
| AVG = 46.9 | 159 | 80 | 79 | 49.7 |
| STD = 1.6 | 151 | 81 | 70 | 46.4 |
|  | 150 | 81 | 69 | 46.0 |
|  | 135 | 71 | 64 | 47.4 |
| MINERAL OIL - RT | 139 | 113 | 26 | 18.7 |
| AVG = 23.1 | 141 | 109 | 32 | 22.7 |
| STD = 2.9 | 133 | 97 | 36 | 27.1 |
|  | 134 | 100 | 34 | 25.4 |
|  | 140 | 110 | 30 | 21.4 |
| MINERAL OIL-130° C. | 128 | 88 | 40 | 31.3 |
| AVG = 35.0 | 127 | 85 | 42 | 33.1 |
| STD = 2.3 | 138 | 89 | 49 | 35.5 |
|  | 140 | 88 | 52 | 37.1 |
|  | 143 | 89 | 54 | 37.8 |
|  | 144 | 93 | 51 | 35.4 |
| WATER SATURATED | 152 | 120 | 32 | 21.1 |
| AVG = 21.2 | 147 | 115 | 32 | 21.8 |
| STD = 0.8 | 149 | 118 | 31 | 20.8 |
|  | 144 | 115 | 29 | 20.1 |
|  | 148 | 115 | 33 | 22.3 |
| TEFLON COATED | 140 | 109 | 31 | 22.1 |
| AVG = 21.4 | 144 | 115 | 29 | 20.1 |
| STD = 0.8 | 139 | 110 | 29 | 20.9 |
|  | 142 | 111 | 31 | 2.18 |
|  | 141 | 110 | 31 | 22.0 |

*standard deviation

TABLE 3

MEASUREMENT OF SAMPLE WIDTH BEFORE TESTING AND AT BREAK

| SAMPLE | Initial Width (mm) | Break Width (mm) | Diff. (mm) | Percent Neck-down |
|---|---|---|---|---|
| MELTBLOWN: UNBONDED | | | | |
| AS IS - RT | 163 | 142 | 21 | 12.9 |
| AVG = 11.0 | 155 | 140 | 15 | 9.7 |
| STD = 2.9 | 154 | 130 | 24 | 15.6 |
|  | 151 | 140 | 11 | 7.3 |
|  | 155 | 140 | 15 | 9.7 |
| AS IS 90° C. | 145 | 95 | 50 | 34.5 |
| AVG = 38.9 | 141 | 85 | 56 | 39.7 |
| STD = 2.4 | 143 | 84 | 59 | 41.3 |
|  | 146 | 90 | 56 | 38.4 |
|  | 153 | 91 | 62 | 40.5 |
| AS IS 130° C. | 142 | 77 | 65 | 45.8 |
| AVG = 46.4 | 144 | 75 | 69 | 47.9 |
| STD = 3.1 | 143 | 74 | 69 | 48.3 |
|  | 140 | 71 | 69 | 49.3 |
|  | 143 | 85 | 58 | 40.6 |
| MINERAL OIL - RT | 155 | 142 | 13 | 8.4 |
| AVG = 10.2 | 163 | 143 | 20 | 12.3 |
| STD = 1.7 | 162 | 145 | 17 | 10.5 |
|  | 162 | 143 | 19 | 11.7 |
|  | 158 | 145 | 13 | 8.2 |

TABLE 2

| SAMPLE NUMBER | | PEAK LOAD (gm) | BREAK LOAD (gm) | PEAK ELONG (in) | BREAK ELONG (in) | PEAK TEA (gm-in) | BREAK TEA (gm-in) |
|---|---|---|---|---|---|---|---|
| MELTBLOWN: BONDED | | | | | | | |
| AS IS - RT | AVG. | 2770 | 1016 | 0.8392 | 0.9842 | 1618.3 | 1948.6 |
|  | STD. | 127 | 61 | 0.1375 | 0.1373 | 359.5 | 359.6 |
| AS IS 90° C. | AVG. | 2022 | 843 | 3.6399 | 3.7288 | 5264.8 | 5420.8 |
|  | STD. | 153 | 59 | 0.4252 | 0.4113 | 847.2 | 839.7 |
| AS IS 130° C. | AVG. | 1459 | 557 | 4.6752 | 4.7496 | 4877.6 | 4957.6 |
|  | STD. | 24 | 40 | 0.2054 | 0.2012 | 448.9 | 447.9 |
| MINERAL OIL - RT | AVG. | 1855 | 652 | Q.9272 | 1.2918 | 1244.4 | 1755.8 |
|  | STD. | 89 | 31 | 0.0910 | 0.0611 | 132.7 | 81.8 |
| MINERAL OIL 130° C. | AVG. | 498 | 369 | 3.3330 | 3.4141 | 1009.1 | 1032.3 |
|  | STD. | 114 | 54 | 0.4348 | 0.4742 | 338.8 | 379.6 |
| TEFLON COAT - RT | AVG. | 2176 | 1052 | 0.9490 | 1.0722 | 1449.2 | 1738.5 |
|  | STD. | 45 | 322 | 0.1623 | 0.1588 | 308.1 | 280.9 |
| WATER SAT. - RT | AVG. | 2775 | 1610 | 0.8173 | 1.0523 | 1621.4 | 2115.4 |
|  | STD. | 272 | 694 | 0.0612 | 0.1285 | 286.1 | 243.8 |

TABLE 4

| SAMPLE NUMBER | | PEAK LOAD (gm) | BREAK LOAD (gm) | PEAK ELONG (in) | BREAK ELONG (in) | PEAK TEA (gm-in) | BREAK TEA (gm-in) |
|---|---|---|---|---|---|---|---|
| MELTBLOWN: UNBONDED | | | | | | | |
| AS IS - RT | AVG. | 4927 | 1957 | 0.3735 | 0.4460 | 1132.0 | 1421.0 |
| | STD. | 169 | 317 | 0.0544 | 0.0731 | 255.7 | 358.0 |
| AS IS 90° C. | AVG. | 3835 | 1535 | 2.3620 | 2.9180 | 7249.0 | 8982.0 |
| | STD. | 270 | 220 | 0.5180 | 0.4030 | 2044.0 | 1163.0 |
| AS IS 130° C. | AVG. | 2277 | 851 | 3.5900 | 4.0140 | 6232.0 | 7354.0 |
| | STD. | 77 | 56 | 0.6845 | 0.8080 | 1486.2 | 1677.0 |
| MINERAL OIL - RT | AVG. | 5139 | 1852 | 0.2922 | 0.4108 | 836.7 | 1295.0 |
| | STD. | 62 | 95 | 0.0385 | 0.0457 | 113.0 | 169.0 |

TABLE 5

| Tensile Property | | Temperature | | | | | | |
|---|---|---|---|---|---|---|---|---|
| | | 30° C. | 55° C. | 82° C. | 95° C. | 105° C. | 130° C. | 150° C. |
| Neck-down @ Break | | 10.7 | 21.3 | 29.4 | 36.1 | 39.1 | 48.5 | 45.4 |
| Elongation @ Peak Load | AVG. | 9.3 | 22.2 | 35.0 | 66.5 | 95.3 | 152 | 112.5 |
| | STD. | 0.8 | 7.5 | 7.3 | 5.4 | 19 | 6 | 12.4 |
| Elongation @ Break | AVG. | 14.5 | 26.3 | 41.3 | 77.3 | 105.4 | 164 | 132 |
| | STD. | 2.1 | 8 | 7.3 | 7.7 | 19 | 14 | 25 |
| Peak Load (grams) | AVG. | 4845 | 4460 | 3995 | 3877 | 3726 | 2577 | 1703 |
| | STD. | 68 | 283 | 172 | 103 | 183 | 68 | 107 |
| Load at Break (grams) | AVG. | 1757 | 1722 | 1617 | 1478 | 1443 | 957 | 649 |
| | STD. | 96 | 231 | 173 | 147 | 65 | 34 | 112 |
| Break Total Energy Absorbed | AVG. | 1248 | 2501 | 3799 | 7480 | 9676 | 10080 | 5393 |
| | STD. | 148 | 760 | 883 | 846 | 1952 | 1341 | 1090 |
| Peak Total Energy Absorbed | AVG. | 733 | 2042 | 3124 | 6289 | 8630 | 9188 | 4442 |
| | STD. | 107 | 716 | 838 | 598 | 2033 | 336 | 283 |

It was found that heating the samples before applying the tensioning force, either with or without an additive, had a significant effect on almost all of the measured variables. Generally speaking, it was found that stretch and recovery properties could be imparted to the barrier fabrics (i.e., nonwoven webs of meltblown polypropylene fibers) without diminishing their barrier properties by heating the nonwoven webs of polypropylene fibers to a temperature at which the peak total energy absorbed by the nonwoven web of meltblown polypropylene fibers is at least about 250 percent greater than the amount absorbed by the nonwoven web of meltblown polypropylene fibers at room temperature; applying a tensioning force to neck the heated nonwoven web; and cooling the necked nonwoven web.

It was found to be desirable to heat the nonwoven web of meltblown polypropylene fibers to a temperature at which the peak total energy absorbed by the nonwoven web is at least about 275 percent greater than the amount absorbed by the nonwoven web at room temperature. For example, the nonwoven web of meltblown polypropylene fibers can be heated to a temperature at which the peak total energy absorbed by the nonwoven web is from about 300 percent greater to more than about 1000 percent greater than the amount absorbed by the nonwoven web at room temperature.

Figure 18:
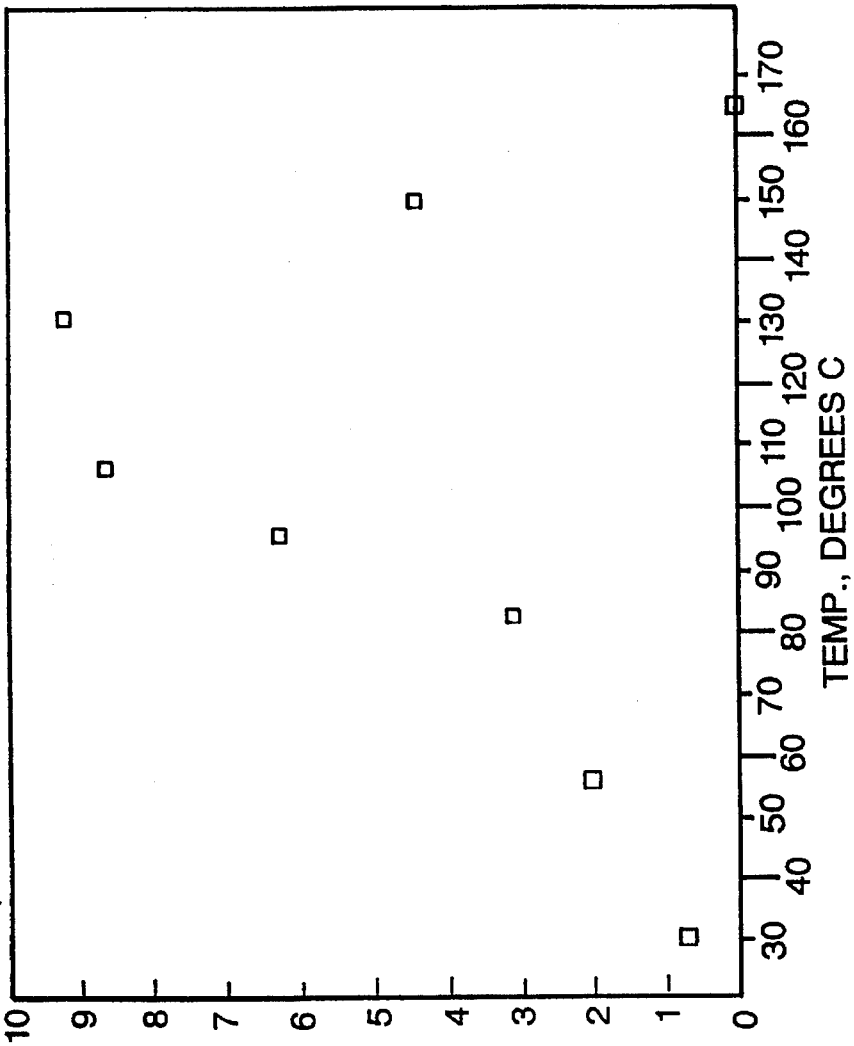
FIG. 18 is a graph of temperature versus total energy absorbed at peak load measured during heat treatment of an exemplary stretchable barrier material.

Heating significantly decreased peak load while it significantly increased peak elongation (enough to increase toughness or TEA) and neck-down. The increased toughness for the samples at higher temperatures indicates decreased process sensitivity. Only a little amount of excess energy is needed to break the web at room temperature while the web is much more forgiving at elevated temperatures. The effects of heating are evident from FIG. 18 which is a graph of temperature versus total energy absorbed at peak load plotted from data taken from Table 5 for the unbonded nonwoven web of meltblown polypropylene. In FIG. 18, it was assumed that the nonwoven web of meltblown polypropylene heated to the melting point of polypropylene (i.e. 165° C.) would have no measurable value for Peak Total Energy Absorbed.

Generally speaking, this range of temperatures at which the Peak Total Energy Absorbed is increased (i.e., increased toughness) is believed to approximately correspond to temperatures ranging from greater than the polypropylene's $\alpha$-transition to about 10 percent below polypropylene's onset of melting at a liquid fraction of 5 percent.

There appears to be a correlation between peak elongation and percent neck-down which indicates a diminishing return of elongating or drawing the sample to get increased amounts of neck-down.

It was found that additives put on the fibers (e.g., Teflon® (polytetrafluroethylene in the form of Scotchguard®) or in the web (e.g., mineral oil) which would lubricate the fibers to reduce interfiber friction reduced peak loads about 30 percent while increasing peak-elongation about 10 percent for the bonded samples. The neck-down was not significantly affected. Saturating the bonded sample with the surfactant solution had essentially no effect on any property.

EXAMPLE 2

Specific physical properties were measured for a control sample and a stretchable meltblown barrier fabric. The control barrier fabric was a 51 gsm unbonded nonwoven web of meltblown polypropylene fibers. That material was heated to 230° F. (110° C.) and then necked-down about 30 percent to make the stretchable barrier fabric.

Cup crush test measurements were made to determine the flexibility of the sample. The cup crush test evaluates fabric stiffness by measuring the peak load required for a 4.5 cm diameter hemispherically shaped foot to crush a 9"×9" piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. The foot and the cup are aligned to avoid contact between the cup walls and the foot which might affect the peak load. The peak load is measured while the foot descends at a rate of about 0.25 inches per second (15 inches per minute) utilizing a Model FTD-G-500 load cell (500 gram range) available from the Schaevitz Company, Pennsauken, N.J.

The basis weight of each fabric sample was determined essentially in accordance with Method 5041 of Federal Test Method Standard No. 191A.

The porosity was determined utilizing a Frazier Air Permeability Tester available from the Frazier Precision Instrument Company and measured in accordance with Federal Test Method 5450, Standard No. 191A, except that the sample size was 8"×8" instead of 7"×7". Porosity may be expressed in units of volume per unit time per unit area, for example, (cubic feet per minute) per square foot of material (e.g., $(ft^3/minute)/ft^2$ or $(CFM/ft^2)$).

Measurements were made of the effective equivalent diameter of pores in the barrier fabric. Pore sizes were determined by liquid displacement techniques utilizing a Coulter Porometer and Coulter POROFIL™ test liquid available from Coulter Electronics Limited, Luton, England. The mean flow pore size is determined by wetting a test sample with a liquid having a very low surface tension (i.e., Coulter POROFIL™). Air pressure is applied to one side of the sample. Eventually, as the air pressure is increased, the capillary attraction of the fluid in the largest pores is overcome, forcing the liquid out and allowing air to pass through the sample. With further increases in the air pressure, progressively smaller and smaller holes will clear. A flow versus pressure relationship for the wet sample can be established and compared to the results for the dry sample. The mean flow pore size is measured at the point where the curve representing 50% of the dry sample flow versus pressure intersects the curve representing wet sample flow versus pressure. The diameter of the pore which opens at that particular pressure (i.e., the mean flow pore size) can be determined from the following expression:

Pore Diameter (Microns)=(40τ)/pressure where τ=surface tension of the fluid expressed in units of mN/M; the pressure is the applied pressure expressed in millibars (mbar); and the very low surface tension of the liquid used to wet the sample allows one to assume that the contact angle of the liquid on the sample is about zero.

The particle hold-out efficiency was determined by Inter-Basic Resources, Inc. of Grass Lake, Mich., in accordance with IBR Test Method No. E-217, Revision G (1/15/91). The test determined air filter retention of dry particles suspended in pure air via a single pass challenge test. A concentrate suspension of contaminant was injected into a feed air stream directed to a test sample. The particle size distribution was measured both upstream and down stream of the test filter. Dry contaminant was obtained from the A.C. Spark Plug Division of General Motors Corporation in a Fine Grade (0.09 to 1.0 microns) and a Coarse Grade (1.5 to >10.0 microns). Particle size distribution for Fine Grade particles was determined utilizing a HIAC/Royco 5109 Particle Counting System available from the HIAC/Royco division of Pacific Scientific Company. Particle size distribution for Coarse Grade particles was determined utilizing a HIAC/Royco LD 400 Sensor, S/N 9002-020, available from the HIAC/Royco division of the Pacific Scientific Company. Tests were conducted at room temperature under airflows of 4 and 8 Standard cubic feet per minute through a circular sample having a diameter of about 90 mm.

General properties of the control barrier fabric and the stretchable barrier fabric are presented in Table 5. Tables 6 and 7 contain the results of particle barrier testing of the control barrier material and the stretchable barrier material. Generally speaking, a barrier material having stretch and recovery properties should have particle barrier properties at least as effective the control barrier material.

TABLE 6

|  | Control Unbonded 51 gsm PP MB | Necked-down 30% at 230° F. Surface Temperature |
|---|---|---|
| Hydrostatic Head (cm) | 67 | 72 |
| Bulk (in) | .016 | .021 |
| Cup Crush |  |  |
| (g) | 242 | 187 |
| (g/mm) | 5223 | 3664 |
| Basis Weight (gsm) | 53.2 | 58.7 |
| MD Tensile |  |  |
| Peak Load (lbs) | 7.63 | 7.54 |
| Peak Elong (%) | 14.2 | 6.42 |
| Peak TEA (in. lbs$_f$/in$^2$) | 2.43 | .882 |
| CD Tensile |  |  |
| Peak Load (lbs) | 4.76 | 3.07 |
| Peak Elong (%) | 27.8 | 36.1 |
| Peak TEA (in. lbs$_f$/in$^2$) | 2.93 | 1.68 |
| Frazier Porosity (CFM/ft2) | 31 | 32 |
| Coulter Profiles (microns) |  |  |
| Mean Flow Pore Size | 17.5 | 17.0 |
| % of pores: |  |  |
| <5 microns | 3 | 3 |
| 5 to 10 | 17 | 14 |
| 10 to 15 | 28 | 30 |
| 15 to 20 | 39 | 39 |
| 20 to 25 | 10 | 10 |
| 25 to 30 | 2 | 3 |
| >30 | <1 | <1 |

TABLE 7

| Sample ID | Main Flow SCFM | Port | Particles/70 cc at: (in microns) | | | | | |
|---|---|---|---|---|---|---|---|---|
| | | | 1.5–2.0 | 2.0–3.0 | 3.0–5.0 | 5.0–7.0 | 7.0–10.0 | >10.0 |
| Control | 8 | Upstream | 3704 | 5359 | 5157 | 2452 | 2468 | 4474 |
| Barrier | | Downstream | 3057 | 4202 | 3535 | 1225 | 882 | 378 |
| Fabric | | Efficiency | 17.47 | 21.59 | 31.45 | 50.04 | 64.26 | 91.55 |
| Control | 4 | Upstream | 3207 | 4680 | 4575 | 1828 | 1680 | 8485 |
| Barrier | | Downstream | 87 | 176 | 196 | 140 | 89 | 679 |
| Fabric | | Efficiency | 97.29 | 96.24 | 95.72 | 92.34 | 94.70 | 92.00 |
| Control | 4 | Upstream | 767 | 1173 | 1148 | 484 | 476 | 697 |
| Barrier | | Downstream | 25 | 27 | 28 | 6 | 6 | 4 |
| Fabric | | Efficiency | 96.74 | 97.70 | 97.56 | 98.76 | 98.74 | 99.43 |
| Stretchable | 4 | Upstream | 4117 | 5284 | 4536 | 1850 | 1674 | 3895 |
| Barrier | | Downstream | 19 | 30 | 32 | 12 | 24 | 106 |
| Fabric | | Efficiency | 99.54 | 99.43 | 99.29 | 99.35 | 98.57 | 97.28 |
| Stretchable | 4 | Upstream | 991 | 1446 | 1502 | 711 | 604 | 2580 |
| Barrier | | Downstream | 11 | 17 | 12 | 11 | 15 | 88 |
| Fabric | | Efficiency | 98.89 | 98.82 | 99.20 | 98.45 | 97.52 | 96.59 |

TABLE 8

| Sample ID | Main Flow SCFM | Port | Particles/0.2 ft3 at: (in microns) | | | | |
|---|---|---|---|---|---|---|---|
| | | | 0.09–0.1 | 0.1–0.2 | 0.2–0.3 | 0.3–0.5 | 0.5–1.0 |
| Control | 4 | Upstream | 20510 | 104946 | 210265 | 108400 | 84144 |
| Barrier | | Downstream | 16997 | 83461 | 142438 | 50937 | 24183 |
| Fabric | | Efficiency | 17.13 | 20.47 | 32.26 | 53.01 | 71.26 |
| Stretchable | 4 | Upstream | 7728 | 34796 | 45316 | 11165 | 4241 |
| Barrier | | Downstream | 3702 | 15620 | 18459 | 3792 | 2016 |
| Fabric | | Efficiency | 52.10 | 55.11 | 59.27 | 66.04 | 76.04 |

EXAMPLE 3

Meltblown and meltblown containing laminates were heated to about 230° F. (110° C.). A tensioning force was applied in the material's machine direction until a 30% loss in width was observed (i.e., until a 30% neck-down was observed). The material was allowed to cool while maintained in the necked-down condition. The resulting material had stretch and recovery properties in the cross-machine direction (i.e., perpendicular to machine direction). Stretch and recovery properties of the materials were measured from 4 inch×6 inch samples of the stretchable material. The 6 inch dimension was in the cross-machine direction and 4 inch dimension was in the machine direction.

Material was mounted in the jaws of an Instron Model 1122 Universal Test Instrument to pull the material in the cross-machine direction (along the 6"length). The gauge length was set at 3 inches and the position of the jaws on the material was marked with lines.

The Instron was set to elongate the material specified distances for particular stretch percentages:
0.3"=10% of initial jaw spacing, or 10% stretch
0.6"=20% of initial law spacing, or 20% stretch
0.9"=30% of initial law spacing, or 30% stretch
1.2"=40% of initial law spacing, or 40% stretch
1.5"=50% of initial law spacing, or 50% stretch
1.8"=60% of initial law spacing, or 60% stretch
2.1"=70% of initial law spacing, or 70% stretch
2.4"=80% of initial law spacing, or 80% stretch
2.7"=90% of initial law spacing, or 90% stretch
3.0"=100% of initial jaw spacing, or 100% stretch A different material sample was elongated to each of the specified distances and then immediately relaxed and removed from the jaws.

Table 8 lists the results of stretch and recovery tests of a nonwoven laminate treated to have stretch and recovery properties. The stretchable barrier fabric was composed of two layers of 18 gsm spunbonded webs sandwiching an 18 gsm nonwoven meltblown fiber barrier fabric. The material had a total basis weight of about 54 gsm. The spunbonded and meltblown fabrics of that particular laminate were formed from an extrudable random copolymer containing from about 3 to about 4 percent, by weight, of ethylene co-monomer and from about 96 to about 97 percent, by weight, propylene.

Some samples were pulled to the maximum stretch length and relaxed three times in the Instron jaws prior to being removed to calculate recovery. These recovery values are reported as "RECOVERY AFTER THREE REPETITIONS". Table 9 lists the results of stretch and recovery tests of an unbonded 51 gsm nonwoven web of meltblown polypropylene fibers treated to have stretch and recovery properties. Table 10 lists the results of stretch and recovery testing for a nonwoven laminate treated to have stretch and recovery properties. The stretchable barrier fabric was composed of two layers of 13.6 gsm spunbonded webs sandwiching an 6.8 gsm nonwoven meltblown fiber barrier fabric. The material had a total basis weight of about 34 gsm. The spunbonded and meltblown fabrics of that particular laminate were formed from an extrudable random copolymer containing from about 3 to about 4 percent, by weight, of ethylene co-monomer and from about 96 to about 97 percent, by weight, propylene.

TABLE 8

|  | Stretch % | % Recovery |
| --- | --- | --- |
| 54 gsm | 10 | 100 |
| Spunbond/Meltblown/ | 20 | 100 |
| Spunbond Laminate | 30 | 100 |
|  | 40 | 100 |
|  | 50 | 100 |
|  | 60 | 93 |
|  | 70 | 88 |
|  | 80 | 82 |

TABLE 9

| Material | Stretch % | First Stretching Average % Recovery | AFTER THREE REPETITIONS Average % Recovery |
| --- | --- | --- | --- |
| 51 gsm | 10 | 100 | 100 |
| Polypropylene | 20 | 97 | 97 |
| Meltblown | 30 | 98 | 100 |

TABLE 10

| Material | Stretch % | First Stretching Average % Recovery | AFTER THREE REPETITIONS Average % Recovery |
| --- | --- | --- | --- |
| 34 gsm | 10 | 100 |  |
| Spunbond/ | 20 | 100 | 97 |
| Meltblown/ | 30 | 98 |  |
| Spunbond | 40 | 96 |  |
| Laminate | 50 | 95 | 89 |
|  | 60 | 94 |  |
|  | 70 | 91 |  |
|  | 80 | 88 | 78 |
|  | 90 | 89 |  |

The present invention is also directed to a disposable protective garment made from the above described stretchable barrier fabric. Generally speaking, the garment may be composed substantially or entirely of the stretchable barrier material. The disposable protective garments of the present invention, having stretch and recovery properties, are particularly well suited for use as protective garments such as, for example, surgical gowns, coveralls, and diapers. Embodiments of the present invention wherein the barrier fabric has uni-directional stretch (i.e., ability to stretch and recover generally in one direction) are particularly well suited for such applications because garments made of such material have dimensional stability for ease of donning and yet provide stretch and recovery properties that adds to the comfort of a wearer. Moreover, the softness and conformability of the stretchable barrier fabric provides a protective garment that fits closely, produces little noise during movement with minimum bagging and tenting, especially after being worn for an extended period.

In most applications, materials adapted to stretch more than about 10 percent and recover to substantially its unstretched dimensions are suitable. For example, materials adapted to stretch from about 13 to 20 percent can be used for coveralls and gowns. In certain applications it may be desirable to use barrier fabrics having a level of stretch much greater than 15 percent, such as, for example, barrier fabrics that can stretch 35 percent or more. It is contemplated that the disposable protective garments of the present invention may contain sections, panels, or portions of barrier fabrics which may have different degrees of stretch and recovery properties. For example, a disposable protective garment may include a body portion of a barrier fabric adapted to stretch about 15 percent and also include attached sleeve portions of a barrier fabric adapted to stretch much more than 15 percent (e.g., about 50 percent or more). It is also contemplated that the sleeve portions or other portions (e.g., leg portions, shoulder portions or back portions of a garment) may include sections of barrier fabrics with very high levels of stretch and recovery properties to provide even greater conformability in the regions of the garment near elbows, knees, shoulders, crotch and other areas where this would be desirable.

In one aspect of the invention, the stretch and recovery properties of the barrier fabric may be non-uniform. This non-uniformity may be intentional or may be caused by limitations of the process equipment. For example, a portion of a barrier fabric may be capable of stretching about 5 to about 15 percent more and/or recovering about 5 to about 15 percent less than another portion of the same material.

An exemplary neckable barrier fabric which could be used for the manufacture of the disposable protective garments of the present invention is nonwoven laminated fabric constructed by bonding together at least one layer of a nonwoven web meltblown fibers (including meltblown microfibers) having stretch and recovery properties with at least one spunbonded continuous filament web. An exemplary three-layer fabric having a first outer ply of a spunbonded web, a middle ply of a meltblown fiber web, and a second outer ply of a spunbonded web may be referred to in shorthand notation as "SMS". Such fabrics are described in U.S. Pat. Nos. 4,041,203, 4,374,888, and 4,753,843, the contents of which are incorporated herein by reference. Those patents are assigned to Kimberly-Clark Corporation, the assignee of the present invention.

To improve resistance to liquid and reduce static buildup, the material may also be treated with compositions such as Zepel® and Zelec® K-C, available from E. I. du Pont De Nemours.

Figure 19:
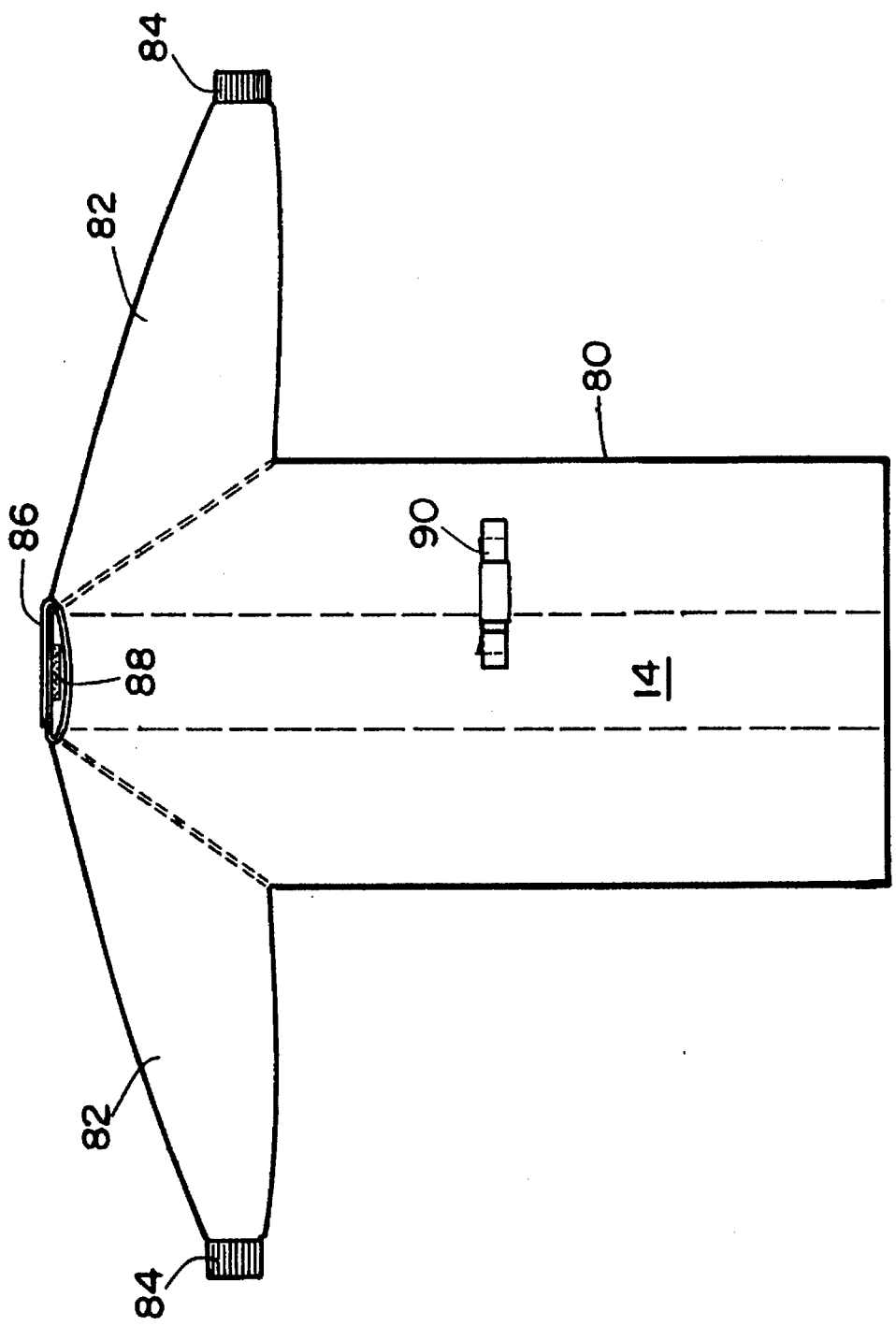
FIG. 19 illustrates an exemplary disposable protective garment.

FIG. 19 illustrates an exemplary disposable surgical gown 80 of the present invention which is adapted to conform to the body of a wearer and which is made from a stretchable barrier fabric. The manufacture of such a gown may be in accordance with known automated, semi-automated, or hand assembly procedures. An example is set forth in U.S. Pat. No. 3,570,012 to Winters, incorporated herein and assigned to the assignee of the present invention. As shown, the gown 80 includes sleeves 82, cuffs 84, neck opening 86 including closure means 88, overlapping back panels, and a belt 90 for closing the gown. The sleeves 82 may be oriented so that the stretch direction of the stretchable barrier fabric may be either parallel or transverse to the direction of motion (i.e., the length) of the sleeve 82. Each configuration provides certain advantages. For example, if the stretch direction of the sleeve 82 is oriented to be transverse to the direction of motion (i.e., length), the dimensional stability of the sleeve is especially well suited to closed-glove suit up procedures.

The materials described above are also well suited for use in the construction of disposable personal care products such as, for example, disposable diapers and disposable incontinence products which are adapted to conform to the body of a wearer. The materials are especially well suited as an outer layer for disposable diapers which is comfortable and conformable but retains liquids within the confines of the diaper.

Figure 20:
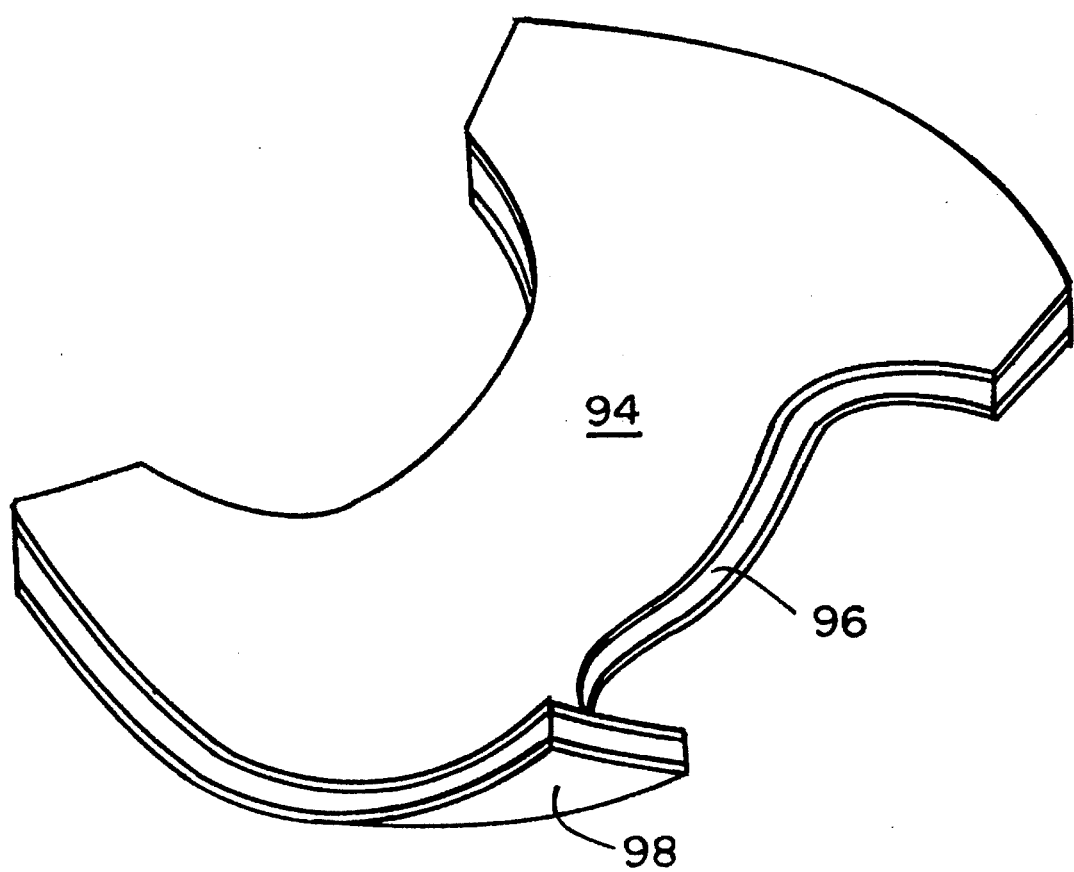
FIG. 20 illustrates an exemplary disposable personal care garment.

FIG. 20 schematically illustrates an exemplary disposable diaper or incontinence product 92 that includes a liner 94, an absorbent medium 96 and a backing material 98. Desirably, the backing material 98 is a stretchable barrier fabric as described above and is adapted to conform to the body of a wearer. Exemplary disposable diapers and incontinence products are set forth in U.S. Pat. Nos. 3,520,303, 4,701,171, 4,747,846 and 4,756,709 assigned to the assignee of the present invention and incorporated herein by reference.

Figure 21:
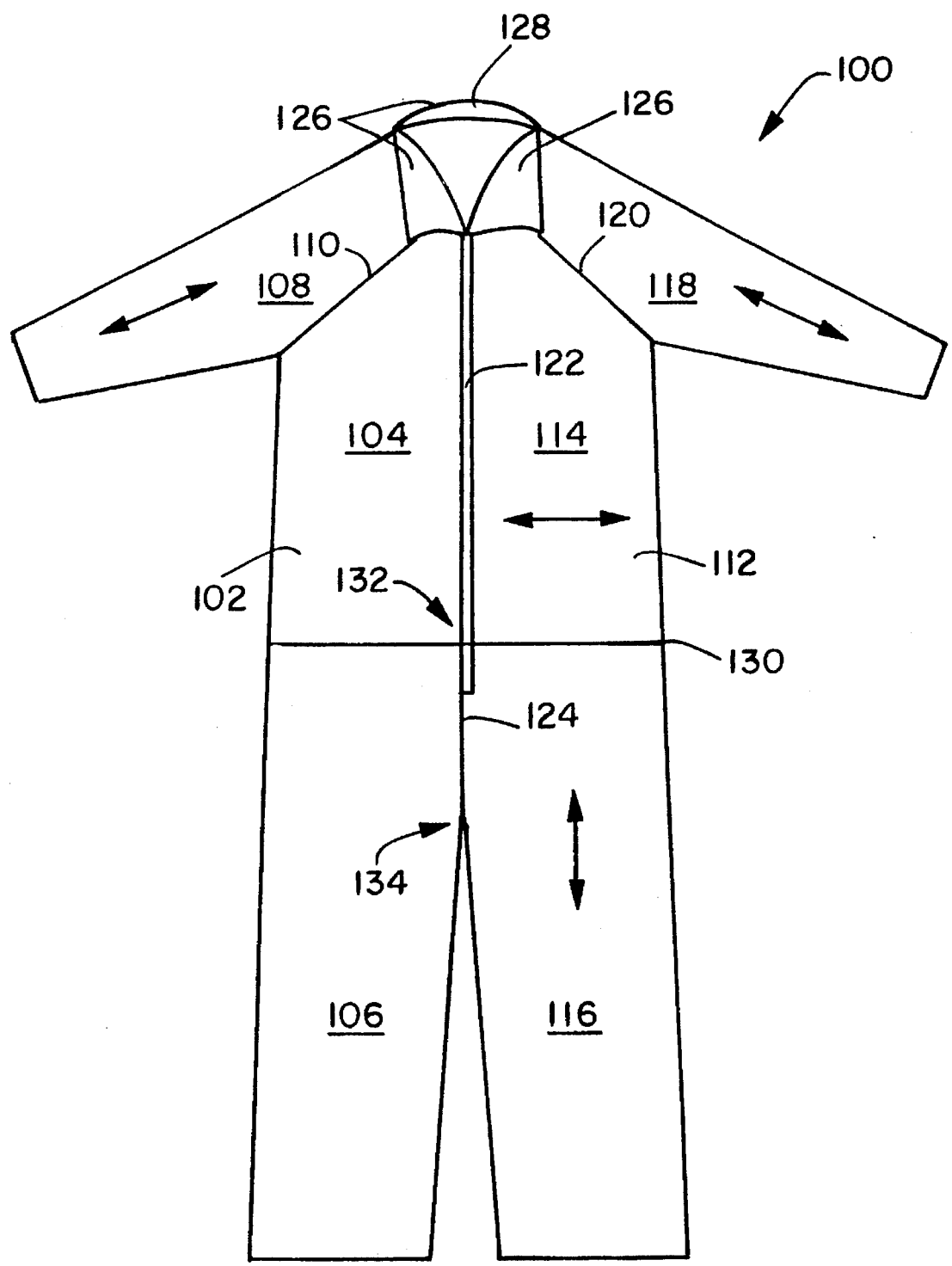
FIG. 21 illustrates exemplary disposable protective coveralls.

FIG. 21 schematically illustrates exemplary disposable protective coveralls 100 of the present invention which are adapted to conform to the body of a wearer. The coveralls 100 contain a left panel 102 which includes a left body portion 104 and a left leg portion 106. The coveralls contain a left sleeve portion 108 which is joined to the left panel 102 by a seam 110. The coveralls also contain a right panel 112 which includes a right body portion 114 and a right leg portion 116. The coveralls contain a right sleeve portion 118 which is joined to the right panel 112 by a seam 120. The left panel 102 and the right panel are joined by a zipper closure 122 and a seam 124. A collar 126 is attached by a seam 128. Desirably, left panel 102 and right panel 112 are constructed so that seam 130 joins an upper half 132 and a lower half 134. The direction of stretch of the barrier fabric in the upper half 132 corresponds to the direction indicated by the arrows associated therewith. The direction of stretch of the barrier fabric in the lower half 134 corresponds to the direction indicated by the arrows associated therewith. Similarly, a desired stretch direction of sleeve portions 108 and 118 corresponds to the direction indicated by the arrows associated therewith. Differing constructions are contemplated and various seams and panels of other possible constructions are not shown. An exemplary coverall is set forth in U.S. Pat. No. 4,670,913, assigned to the assignee of the present invention and incorporated herein by reference.

The foregoing description relates to preferred embodiments of the present invention, modifications or alterations may be made without departing from the spirit and scope of the invention as defined in the following claims.

What is claimed is:

1. A method of producing a stretchable nonwoven barrier fabric, the method comprising:
   heating a nonwoven web comprising non-elastomeric meltblown thermoplastic polymer fibers to a temperature at which the peak total energy absorbed by the web is at least about 250 percent greater than the amount absorbed by the web at room temperature;
   applying a tensioning force to neck the heated nonwoven web; and
   cooling the necked nonwoven web, whereby said web is characterized by a pore size distribution and mean flow pore size which are substantially unchanged by said heating, tensioning and cooling.

2. The method of claim 1 wherein the meltblown thermoplastic polymer fibers comprise a polymer selected from the group consisting of polyolefins, polyesters, and polyamides.

3. The method of claim 2 wherein the polyolefin is selected from the group consisting of one or more of polyethylene, polypropylene, polybutene, ethylene copolymers, propylene copolymers, and butene copolymers.

4. The method of claim 3 wherein the meltblown thermoplastic polymer fibers comprise meltblown polyolefin fibers and a nonwoven web of such fibers is heated to a temperature ranging from greater than the polymer's α-transition to about 10 percent below the onset of melting at a liquid fraction of 5 percent.

5. The method of claim 3 wherein the meltblown thermoplastic polymer fibers comprises meltblown polypropylene fibers and a nonwoven web of such fibers is heated to a temperature ranging from about 105 to about 145 degrees Centigrade.

6. The method of claim 6 wherein a nonwoven web of meltblown polypropylene fibers is heated to a temperature ranging from about 110 to about 140 degrees Centigrade.

7. The method of claim 5 wherein a nonwoven web of meltblown polypropylene fibers is heated to a temperature ranging from about 120 to about 125 degrees Centigrade.

8. The method of claim 1 wherein the tensioning force is sufficient to neck the nonwoven web to a necked width that is at least about 10 percent less than the width of the nonwoven web before application of the tensioning force.

9. The method of claim 8 wherein the tensioning force is sufficient to neck the nonwoven web to a necked width that is from about 15 percent to about 50 percent less than the width of the nonwoven web before application of the tensioning force.

10. The method of claim 1 wherein the nonwoven web is heated by infra-red radiation, steam cans, microwaves, ultrasonic energy, flame, hot gases, and hot liquid.

11. A stretchable nonwoven barrier fabric comprising at least one web of non-elastomeric meltblown thermoplastic polymer fibers, the barrier fabric having been heated and then necked so that it is adapted to stretch at least about 10 percent more than an identical untreated nonwoven web of meltblown fibers, whereby said fabric is characterized by a pore size distribution and mean flow pore size which are substantially unchanged by said heating and necking.

12. The stretchable barrier fabric of claim 11 wherein the stretchable barrier fabric is adapted to stretch from about 15 percent to about 60 percent and recover at least about 70 percent when stretched 60 percent.

13. The stretchable barrier fabric of claim 12 wherein the stretchable barrier fabric is adapted to stretch from about 20 percent to about 30 percent and recover at least about 75 percent when stretched 30 percent.

14. The stretchable barrier fabric of claim 11 wherein the fabric provides resistance to water penetration as measured by a hydrostatic head of at least about 30 cm.

15. The stretchable barrier fabric of claim 14 wherein the hydrostatic head ranges from about 35 to about 120 cm.

16. The stretchable barrier fabric of claim 15 wherein the hydrostatic head ranges from about 40 to about 90 cm.

17. The stretchable barrier fabric of claim 11 wherein the fabric provides a particle holdout efficiency of at least about 40 percent for particles having an average diameter of greater than about 0.1 micron.

18. The stretchable barrier fabric of claim 11 wherein the fabric provides a particle holdout efficiency of at least about 50 percent for particles having an average diameter of greater than about 0.1 micron.

19. The stretchable barrier fabric of claim 11 wherein the fabric provides a particle holdout efficiency of at least about 95 percent for particles having an average diameter of greater than about 1.5 microns.

20. The stretchable barrier fabric of claim 11 wherein the meltblown fibers include meltblown microfibers.

21. The stretchable barrier fabric of claim 20 wherein the at least about 50 percent, as determined by optical image analysis, of the meltblown microfibers have an average diameter of less than 5 microns.

22. The stretchable barrier fabric of claim 11 wherein the non-elastomeric meltblown thermoplastic polymer fibers comprise a polymer selected from the group consisting of polyolefins, polyesters, and polyamides.

23. The stretchable barrier fabric of claim 22 wherein the polyolefin is selected from the group consisting of one or more of polyethylene, polypropylene, polybutene, ethylene copolymers, propylene copolymers, and butene copolymers.

24. The stretchable barrier fabric of claim 11 wherein the nonwoven web of non-elastomeric meltblown thermoplastic polymer fibers further includes one or more secondary materials selected from the group consisting of textile fibers, wood pulp fibers, particulates and super-absorbent materials.

25. The stretchable barrier fabric of claim 11 wherein the nonwoven web has a basis weight of from about 6 to about 400 grams per square meter.

26. A multilayer material comprising at least one layer of the stretchable barrier fabric according to claim 11 and at least one other layer.

27. The multilayer material of claim 26 wherein the other layer is selected from the group consisting of woven fabrics, knit fabrics, bonded carded webs, continuous spunbond filament webs, meltblown fiber webs, and combinations thereof.

28. A disposable protective garment comprising generally planar sections joined by seams, at least one of the sections being composed of a nonwoven material comprising at least one layer of the stretchable barrier fabric according to claim 11.

29. The disposable protective garment of claim 28, the garment being protective coveralls having a body portion, sleeve portions and leg portions extending therefrom and in which the stretch and recovery properties of the barrier fabric is parallel to the direction of motion of at least one of said body portion, sleeve portions or leg portions.

30. The disposable protective garment of claim 28, the garment being a gown having a body portion and sleeve portions extending therefrom and in which the stretch and recovery properties of the barrier fabric is parallel to the direction of motion of at least one of said body portion or sleeve portions.

31. The disposable protective garment of claim 28, the garment being a protective suit comprising:

a top section comprising a body portion and sleeve portions extending therefrom, and a bottom section comprising leg portions.

* * * * *

UNITED STATES PATENT AND TRADEMARK OFFICE
CERTIFICATE OF CORRECTION

PATENT NO. : 5,492,753
DATED : February 20, 1996
INVENTOR(S) : Levy et al

It is certified that error appears in the above-indentified patent and that said Letters Patent is hereby corrected as shown below:

Column 15, table 2, line 59, "Q.9272" should read --0.9272--;
Column 17, table 5, line 20, "Neck-down" should read --Neck-down (%)--;
Column 17, table 5, line 22, "Elongation" should read --Elongation (%)--;
Column 17, table 5, line 24, "Elongation" should read --Elongation (%)--;
Column 21, line 56, "law" should read --jaw--;
Column 21, line 57, "law" should read --jaw--;
Column 21, line 58, "law" should read --jaw--;
Column 21, line 59, "law" should read --jaw--;
Column 21, line 60, "law" should read --jaw--;
Column 21, line 61, "law" should read --jaw--;
Column 21, line 62, "law" should read --jaw--;
Column 21, line 63, "law" should read --jaw--;
Column 20, line 23, "Table 5" should read --Table 6--;
Column 20, line 23, "Table 6" should read --Table 7--;
Column 20, line 24, "Table 7" should read --Table 8--.
Column 22, line 35, "Table 8" should read --Table 9--;
Column 22, line 52, "Table 9" should read --Table 10--;
Column 22, line 55, "Table 10" should read --Table 11--;
Column 23, line 2, "Table 8" should read --Table 9--;
Column 23, line 14, "Table 9" should read --Table 10--;

UNITED STATES PATENT AND TRADEMARK OFFICE
CERTIFICATE OF CORRECTION

PATENT NO. : 5,492,753
DATED : February 20, 1996
INVENTOR(S) : Levy et al

It is certified that error appears in the above-indentified patent and that said Letters Patent is hereby corrected as shown below:

Column 23, line 24, "Table 10" should read --Table 11--.

Signed and Sealed this

Twenty-first Day of January, 1997

Attest:

BRUCE LEHMAN

Attesting Officer

Commissioner of Patents and Trademarks